(12) United States Patent
Herlyn et al.

(10) Patent No.: US 6,486,133 B1
(45) Date of Patent: Nov. 26, 2002

(54) METHODS FOR INDUCING LOCALIZED VASCULAR DEVELOPMENT AND ENHANCING THE REPAIR OF A WOUND IN THE MAMMAMIAN DERMIS

(75) Inventors: Meenhard Herlyn, Wynnewood, PA (US); Mark Nesbit, Palmyra, NJ (US); Kapaettu Satyamoorthy, Swarthmore, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 0 days.

(21) Appl. No.: 09/380,124

(22) PCT Filed: Mar. 6, 1998

(86) PCT No.: PCT/US98/04487
§ 371 (c)(1),
(2), (4) Date: Aug. 25, 1999

(87) PCT Pub. No.: WO98/39035
PCT Pub. Date: Sep. 11, 1998

Related U.S. Application Data
(60) Provisional application No. 60/040,042, filed on Mar. 7, 1997.

(51) Int. Cl.$^7$ .................. A61K 48/00; C12N 15/63; C12N 15/86; C12N 15/00
(52) U.S. Cl. .................. 514/44; 435/455; 435/456; 435/320.1
(58) Field of Search ................ 514/44; 424/93.2, 424/93.21; 435/320.1, 455, 456

(56) References Cited

U.S. PATENT DOCUMENTS

| | | | |
|---|---|---|---|
| 5,073,492 A | 12/1991 | Chen et al. | 435/240.2 |
| 5,194,596 A | 3/1993 | Tischer et al. | 530/399 |
| 5,219,739 A | 6/1993 | Tischer et al. | 435/69.4 |
| 5,480,975 A | 1/1996 | Goldberg | |
| 5,661,132 A * | 8/1997 | Eriksson et al. | 514/44 |
| 5,731,190 A | 3/1998 | Wickham et al. | 435/320.1 |
| 5,792,453 A | 8/1998 | Hammond et al. | 424/93.21 |
| 5,869,037 A * | 2/1999 | Crystal et al. | 424/93.2 |
| 5,932,540 A | 8/1999 | Hu | |
| 5,962,427 A * | 10/1999 | Goldstein et al. | 514/44 |
| 5,980,887 A | 11/1999 | Isner | |
| 6,040,157 A | 3/2000 | Hu | |
| 6,121,246 A * | 9/2000 | Isner | 514/44 |
| 6,187,767 B1 * | 2/2001 | Araneo et al. | 514/178 |

FOREIGN PATENT DOCUMENTS

| | | |
|---|---|---|
| EP | 476983 A1 | 3/1992 |
| EP | 476 983 | 3/1992 |
| EP | 506 477 | 9/1992 |
| EP | 550296 A2 | 7/1993 |
| EP | 550 296 | 7/1993 |
| EP | 506477 A2 | 6/1999 |
| WO | WO95/04142 A2 | 2/1995 |
| WO | WO 95/24473 * | 9/1995 |
| WO | WO95/32708 A1 | 12/1995 |
| WO | WO96/23065 A2 | 8/1996 |
| WO | WO96/26736 A1 | 9/1996 |
| WO | WO 96/26742 * | 9/1996 |
| WO | WO96/27006 A2 | 9/1996 |
| WO | WO 96/39508 * | 12/1996 |
| WO | WO 96/39515 * | 12/1996 |
| WO | WO 97/12050 * | 4/1997 |
| WO | WO97/12050 A1 | 4/1997 |
| WO | WO 97/13857 * | 4/1997 |
| WO | WO97/13857 A1 | 4/1997 |
| WO | WO 97/38729 * | 10/1997 |
| WO | WO98/38729 A1 | 10/1997 |
| WO | WO98/19712 A1 | 5/1998 |
| WO | WO99/46364 A1 | 9/1999 |

OTHER PUBLICATIONS

Thomas, Cyclopedic Medical Dictionary, 1993, 1808–1811.*
N. Miller et al.,"Targeted Vectors for Gene Therapy", FASEB J., 9:190–199, (Feb. 1995).*
M. Deonarain, Ligand–targeted receptor–mediated vectors for gene delivery. Exp.Opin. Ther. Patents 8:53–69, 1998.*
I. Verma, Gene Therapy–Promises, Problems and Prospects. Nature 389:239–242, (Sep. 18, 1997).*
C. Magovern, et al. Regional Angiogenesis Induced in Nonischemic Tissue by an Adenoviral Vector Expressing Vascular Endothelial Growth Factor. Hum. Gene Ther. 8:215–227, 1997.*
Y.Setoguchi et al., "Ex Vivo and In Vivo Gene Transfer to the Skin Using Replication–Deficient Recombinant Adenovirus Vectors", J. Invest. Dermatol. 102:415–421, 1994.*
S. Takeshita et al., "Gene Transfer of Naked DNA Encoding for Three Isoforms of Vascular Endothelial Growth Factor Stimulates Collateral Development in vivo", *Lab. Invest.*, 75 (4):487–501 (Oct. 1996).
A. Harris et al., "Gene Therapy Through Signal Transduction Pathways and Angiogenic Growth Factors as Therapeutic Targets in Breast Cancer", *Cancer*, 74 (3S):1021–1025 (Aug. 1994).

(List continued on next page.)

*Primary Examiner*—Dave T. Nguyen
*Assistant Examiner*—Quang Nguyen
(74) *Attorney, Agent, or Firm*—Howson and Howson

(57) ABSTRACT

A method for repairing defects and inducing vascularization in mammalian tissue, preferably skin, involves administering to the tissue a recombinant replication defective virus, preferably adenovirus, carrying a selected growth factor gene, preferably VEGF or PDGF, under operative control of regulatory sequences which direct the expression of the growth factor(s). Also provided is a method for infecting a tissue to be transplanted with such recombinant adenoviruses prior to transplantation and, as a composition, an infected culture of human tissue to be transplanted which is infused with a selected growth factor prior to transplantation. Screening methods for the treatment of angiogenic disorders, e.g., hemangiomas and cancers, also employ an animal model on which is engrafted a full thickness human tissue infused with a growth factor.

4 Claims, 6 Drawing Sheets

OTHER PUBLICATIONS

J. Mühihauser et al., "VEGF165 Expressed by a Replication Deficient Recombinant Adenovirus Vector Unduces Angiogenesis in vivo", *Cir. Res.*, 77 (6):1077–1086 (December 1995).

B.Péault et al., "Gene Transfer to Human Fetal Pulmonary Tissue Developed in Immunodeficient SCID Mice", Human Gene Therapy, 5 (9):1131–1137 (Sept. 1994).

B. Allen–Hoffman et al., "Fibronectin Levels are Enhanced in Human Fibroblasts Overexpressing the c–sis Protooncogene", *J. Biol. Chem.*, 265 (9):5219–5222 (Mar. 25, 1990).

M. Bywater et al., "Expression of Recombinant Platelet Derived Growth Factor A–and B–Chain Homodimers in Rat–1 Cells and Human Fibroblasts Reveals Differences in Protein Processing and Autocrine Effects", *Mol. Cell. Biol.*, 8 (7):2753–2762 (Jul. 1988).*

P. Soballe et al., "Carcinogenesis in Human Ski Grafted to SCID Mice", *Can. Res.*, 56:757–764 (Feb. 15, 1996).*

Alberts et al., Molecular Biology of the Cell, 1994, P.1140.*

S. Eming et al., "Genetically Modified Human Epidermis Over expressing PDGF–A directs the Development of a Cellular and Vascular connective Tissue Stroma when Transplanted to Athymic Mice–Implications for the Use of Genetically Modified Keratinocytes to Modulate Dermal Regeneration", J. Invest. Dermatol, 105(6):756–763 (Dec. 1995).

C. Thomas, Taber's Cyclopedic Medical Dictionary, Edition 17, pp. 1808–1811 (1993).

C. Magovern et al., "Direct In Vivo Gene Transfer to Canine Myocardium Using a Replication–Deficient Adenovirus Vector", Ann. Thorac. Surg., 62(2):425–434 (Aug. 1996).

C. Chen et al., "High–Efficiency Transformation of Mammalian Cells by Plasmid DNA", Mol. Cell. Biol., 7(8):2745–2752 (Aug. 1987).

D. Greenhalgh et al., "PDGF and FGF Stimulate Wound Healing in the Genetically Diabetic Mouse", American Journal of Pathology, 136(6):1235–1246 (June, 1990).

T. Mustoe et al., "A Phase II Study to Evaluate Recombinant Platelet–Derived Growth Factor–BB in the Treatment of Stage 3 and 4 Pressure Ulcers", Arch. Surg., 129:213–219 (Feb., 1994).

G. Hübner et al., "Differential Regulation of Pro–Inflammatory Cytokines During Wound Healing in Normal and Glucocorticoid–Treated Mice", Cytokine, 8(7):548–556 (Jul., 1996).

C. Andree et al., "In Vivo Transfer and Expression of a Human Epidermal Growth Factor Gene Accelerates Wound Repair", Proc. Natl. Acad. Sci, USA, 91:12188–12192 (Dec., 1994).

G. Krueger et al., "Genetically Modified Skin to Treat Disease: Potential and Limitations", J. Invest. Dermatol., 103:76S–84S (1994).

U. Hengge et al., "Cytokine Gene Expression in Epidermis with Biological Effects Following Injection of Naked DNA", Nature Genetics, 10:161–166 (June, 1995).

S. Benn et al., "Particle–Mediated Gene Transfer with Transforming Growth Factor–βcDNAs Enhances Wound Repair in Rat Skin", J. Clin. Invest., 98(12): 2894–2902 (Dec., 1996).

F. Grinnell, "Wound Repair, Keratinocyte Activation and Integrin Modulation", J. Cell Science, 101:1–5 (Jan., 1992).

V. Falanga et al., "Workshop on the Pathogenesis of Chronic Wounds", M. Invest. Dermatol., 102:125–127 (Jan., 1994).

I. Ciernik et al., "Puncture–Mediated Gene transfer to the Skin", Human Gene Therapy, 7:893–899 (May 20, 1996).

G. Pierce et al., "Detection of Platelet–Derived Growth Factor (PDGF)–AA in Actively Healing Human Wounds Treated wiht Recombinant PDGF–BB and Absence fo PDGF in Chronic Nonhealing Wounds", J. Clin Invest., 96:1336–1350 (Sep., 1995).

I. Ono et al., "Studies on Ctokines Related to Wound Healing in Donor Site Wound Fluid", J. Dermatol, Sci., 10:241–245 (Nov. 1995).

G. Pierce et al., "Detection of Platelet–derived Growth Factor (BB Homodimer), transforming Growth Factor–62 1, and Basic Fibroblast Growth Factor in Dermal Wound Healing", Am. J. Pathol., 140(6):1375–1388 (June, 1992).

S. Lynch et al., "Role of Platelet–derived Growth Factor in Wound Healing: Synergistic Effects with Other Growth Factors", Proc. Natl. Acad. Sci. USA, 84:7696–7700 (Nov., 1987).

D. Steed et al., "Randomized Prospective Double–Blind Trial in Healing Chronic Diabetic Foot Ulcers", Diabetes Care, 15(11):1598–1604 (Nov., 1992).

M. Robson et al., "Recombinant Human Platelet–derived Growth Factor–BB for the Treatment of Chromic Pressure Ulcers", Ann. Plast. Surg., 29:193–201 (Sep., 1992).

G. Pierce et al., "Role of Platelet–Derived Growth Factor in Wound Healing", J. Cell. Biochem., 45:319–326 (Apr., 1991).

R. Ziegelstein et al., "Initial Contact and Subsequent Adhesion of Human Neutrophils or Monocytes to Human Aortic Endothelial Cells Releases an Endothelial Intracellular Calcuim Store", Circulation, 90(4):1899–1907 (Oct., 1994).

* cited by examiner

SEQUENCE LISTING (1) GENERAL INFORMATION:

(iii) NUMBER OF SEQUENCES: 4

(2) INFORMATION FOR SEQ ID NO: 1:

-continued (i) SEQUENCE CHARACTERISTICS:
            (A) LENGTH: 21 base pairs
            (B) TYPE: nucleic acid
            (C) STRANDEDNESS: single
            (D) TOPOLOGY: unknown (ii) MOLECULE TYPE: other nucleic acid
            (A) DESCRIPTION: /desc = "upstream primer hPDGF-B"

(xi) SEQUENCE DESCRIPTION: SEQ ID NO: 1:

TGGGCGCTCT TCCTGTCTCT C                                              21

(2) INFORMATION FOR SEQ ID NO: 2:

(i) SEQUENCE CHARACTERISTICS:
            (A) LENGTH: 21 base pairs
            (B) TYPE: nucleic acid
            (C) STRANDEDNESS: single
            (D) TOPOLOGY: unknown (ii) MOLECULE TYPE: other nucleic acid
            (A) DESCRIPTION: /desc = "downstream primer hPDGF-B"

(xi) SEQUENCE DESCRIPTION: SEQ ID NO: 2:

CTCGGCCCCA TCTTCCTCTC C                                              21

(2) INFORMATION FOR SEQ ID NO: 3:

(i) SEQUENCE CHARACTERISTICS:
            (A) LENGTH: 18 base pairs
            (B) TYPE: nucleic acid
            (C) STRANDEDNESS: single
            (D) TOPOLOGY: unknown (ii) MOLECULE TYPE: other nucleic acid
            (A) DESCRIPTION: /desc = "upstream primer rabbit B-actin"

(xi) SEQUENCE DESCRIPTION: SEQ ID NO: 3:

TGGGCAGAAG GACTCGTA                                                  18

(2) INFORMATION FOR SEQ ID NO: 4:

(i) SEQUENCE CHARACTERISTICS:
            (A) LENGTH: 18 base pairs
            (B) TYPE: nucleic acid
            (C) STRANDEDNESS: single
            (D) TOPOLOGY: unknown (ii) MOLECULE TYPE: other nucleic acid
            (A) DESCRIPTION: /desc = "downstream primer rabbit B-actin"

(xi) SEQUENCE DESCRIPTION: SEQ ID NO: 4:

CGCAGCTCGT TGTAGAAG                                                  18

METHODS FOR INDUCING LOCALIZED VASCULAR DEVELOPMENT AND ENHANCING THE REPAIR OF A WOUND IN THE MAMMAMIAN DERMIS

CROSS-REFERENCE TO RELATED APPLICATIONS

This is a 371 of PCT/US98/04487, which claims the benefit of the priority of U.S. patent application Ser. No. 60/040,042, filed Mar. 7, 1997.

This invention was supported in part by the National Institutes of Health Grant Nos. CA25874, CA47159, and CAI 0815. The United States government has certain rights in this invention.

FIELD OF THE INVENTION

The present invention relates generally to the field of enhancing the repair of wounds in mammalian tissue, e.g., following injury, burn, surgery and skin grafting or tissue transplantation, and inducing neovascularization therein.

BACKGROUND OF THE INVENTION

Wound repair and tissue generation in normal and impaired wound healing conditions is a major focus in medicine. In particular, the capability to achieve wound healing or develop tissue growth in an impaired wound healing, environment remains a problem. The mechanisms of normal wound healing, hypertrophic and keloid scarring, as well as the generation of new tissue growth have been postulated to be related, particularly at the growth factor level. The potential for growth factors to enhance wound healing, soft tissue generation, scar manipulation, and tumor activity has stimulated intense investigative efforts over the past few years. Unfortunately, these studies have yet to provide a clinically effective delivery system or clinically significant results in human skin.

Experimental evidence suggests that human vascular endothelial growth factor (VEGF), for example, has an important function in the maintenance of the vasculature in healthy tissues, in wound healing and in angiogenesis. VEGF is a potent mitogen for endothelial cells, and causes cytoplasmic accumulation of calcium, changes in cell morphology, an increase in cell division, and altered gene expression (up-regulates proteases). VEGF also inhibits the maturation of dendritic cells, permeabilizes vascular beds (VEGF enhances vesicular-vacuolar organelles) and is responsible for the autocrine growth of AIDS-Kaposi sarcoma cells.

At low levels, VEGF is expressed by a variety of normal cells including keratinocytes [C. P. Kiritsy and S. E. Lynch, 1993, *Crit. Rev. Oral Biol. Bed.*, 4:729–760] and macrophages in the healing of cutaneous wounds. VEGF is also found in the endometrium and corpus luteum; is produced by podocytes or renal glomerulus, by prostatic epithelium and by epithelial cells of the adrenal cortex and lung. VEGF is upregulated during wound healing, psoriasis and delayed type hypersensitivity. It is produced by cardiac myocytes in ischemic myocardium and by synovial lining cells in the pannus of rheumatoid arthritis. It is constitutive in many tumors, such as tumors of the colon, stomach, pancreas, kidney, bladder, breast and glioblastoma. Most malignant cells, including melanoma cells, express VEGF. Its expression can be induced by other growth factors, such as transforming growth factor (TGF-β) and platelet derived growth factor (PDGF) and cytokines, or by hypoxic environmental conditions [S. A. Eming el al, 1995, *J. Invest. Dermatol.*, 105:756–763]. Its over expression leads to hypervascularization which is often associated with chronic inflammatory diseases and cancer [see, e.g., F. Grinnel, 1992, *J. Cell Sci.*, 101:1–5, V. Falanga el al, 1994, *J. Invest. Dermatol.*, 102:125–127; G. F. Pierce et al, 1991, *J. Cell. Biol.*, 45:319–326].

A variety of VEGF constructs and uses in neovascularization and wound healing have been proposed. For example, see International Patent Application WO96/26736, published Sep. 6, 1996, which relates to VEGF-B proteins useful to accelerate angiogenesis in wound healing, International Patent Application WO95/24473, published Sep. 14, 1995, relates to VEGF-βpolypeptide, useful for wound healing and periodontal disease; European Patent Application No. 550296, published Jul. 7, 1993 relates to VEGF protein, used for promoting angiogenesis in treatment of cardiac angiopathy, wounds, burn injuries, postoperative tissue damage, etc.; U.S. Pat. No. 5,219,739, issued Jun. 15, 1993, relating to DNA sequences, vectors and transformed cells for producing VEGF for treating wounds European Patent Application No. 506477, published Sep. 30, 1992, relating to VEGF sub-units for inducing tissue repair and growth; European Patent Application No. 476983, published Mar. 25, 1992, and relating to VEGF 11 for coating blood vessels or to promote tissue repair; U.S. Pat. No. 5,073,492, issued Dec. 17, 1991; and U.S. Pat. No. 5,194,596, issued Mar. 16, 1993, among others.

The use of replication deficient adenovirus vectors (Ad) to deliver VEGF to heart, smooth muscle and endothelial cells, as well as delivery of such vectors via subcutaneous injection has been the subject of much experimentation. For example, replication defective adenoviruses carrying VEGF genes have been described in, e.g., J. Muehihauser et al, 1995, *Circul. Res.*, 77(6):1077–1086 and J. Muhlhauser et al, 1994, *J. Cell. Biochem.*, Supp. 0 (18 Part A), p. 239. The Muhlhauser references refer to the delivery of a replication deficient adenovirus carrying a human VEGF-165 gene under the control of the cytomegalovirus promoter to human umbilical vein endothelial cells and rat aorta smooth muscle cells. The same vector was injected subcutaneously in mice, and two weeks post injection, histological evidence of neovascularization in the tissue surrounding the site of injection was observed. Similarly, C. J. Magovern et al, 1996, *Annals Thor. Sure.*, 62(2):425–434 refers to the use of a replication defective Ad carrying the gene for VEGF in direct myocardial injection to accomplish gene transfer. These authors noted sustained and localized expression of VEGF for up to 7 days after a single injection, and posited that this strategy may be used to stimulate angiogenesis in ischemic myocardium [see, also, R. Ziegelstein et a/, 1994, *Circul.*, 90(4), part II, p. 1899].

The principal growth factor found in platelets as well as macrophages, fibroblasts and endothelial cells is platelet derived growth factor (PDGF), a 30 Kda protein dimer existing in three different isoforms (PDGF-AA, PDGF-AB and PDGF-BB), which is released at a site of injury within the body. The mitogenic effects of PDGF-BB isoform, which can bind to the PDGF-β receptor, on fibroblasts, smooth muscle cells and other mesenchymal cells have been extensively documented. The chemoattractive effects mediated through the PDGFB receptor have implicated PDGF-BB and PDGF-AB in the physiologic process of wound healing and tissue repair and the pathologic process of atherosclerosis.

PDGF-BB has been shown to be an integral part of the initial and early stages of wound healing, with its participation in the inflammation and granulation tissue stages respectively. PDGF-BB was also shown to be present in wounds and also within the blister fluid of burn patients. The final stage of wound healing, in which scar tissue remodelling occurs, can largely be attributed to the autocrine production of PDGF-BB from dermal fibroblasts. Such autocrine loops are initially stimulated in a paracrine fashion with platelet PDGF, which ultimately results in the deposition of extracellular molecules such as fibronectin and tenascin. Chondroitin sulfate may also be deposited which may inhibit the action of collagenase. In wound healing it has also been shown that there is also a major reorganization of collagen types I and III. The accumulation of such molecules in connective tissue is associated with diseases such as rheumatoid arthritis and atherosclerosis. This may implicate the involvement of PDGF in the pathogenesis of these diseases. The sequence homology of PDGF-B with a viral oncogene from Simian Sarcoma virus (v-sis), also implicates PDGF-B in normal and neoplastic development, with many tumors being intimately involved with the production of PDGF-BB.

Systematic analyses of the roles of individual growth factors and cytokines for their angiogenic properties have been difficult in disease-related conditions because experimental over expression or suppression of expression of growth factors in human cells could not be achieved consistently under in vivo conditions. Indirect evidence of the potential roles of growth factors came from expression studies in diseased skin in which mRNA or protein levels were determined.

Application of exogenous growth factors to wounds, for example, has shown efficacy in wound healing in some experimental animal models, e.g., topically applied in impaired wounds, but the few clinical studies are difficult to interpret [Kiritsy, cited above], apparently due to the limited biological half life of the growth factors when applied topically or the difficulty of obtaining frequent biopsies for analyses. Only minimal improvement in non-impaired wounds has been shown. For example, PDGF-BB has been applied to chronic wounds such as diabetic ulceration. The efficient penetration of PDGF to cells in the wound bed and a demonstrable healing effect has been difficult to achieve and may be enhanced by wound dressings [Pierce, G. F, et al, 1995 *J. Clin. Invest.*, 96:1336–1350, Ono, I., et al, 1995 *J. Dermatol. Sci.*, 10:241–245]. Up-regulation of proteinases in non-healing wounds may contribute to the rapid degradation of topically applied PDGF [Yager, D. R., et al, 1996 *J. Invest. Dermatol.* 107:743–748]. While exogenous PDGF-B can enhance acute experimental wounds in animals [see, e.g., Lynch, S. E., et al. 1987, *Proc. Natl. Acad. Sci. USA* 84:7696–7700; Pierce, G. F., et al 1991 *Am. J. Pathol.* 138:629–646; Pierce, G. F., 1992, *Am. J. Pathol.* 140:1375–1388], results in human trials of chronic wounds have been less effective [Steed, D. L. et al, 1992, *Diabetes Care.* 15:1598–1604; Robson, M. C., et al, 1992, *Annals Plastic Surg.* 29:193–201], necessitating improved methods for drug delivery. One alternative approach is to express the PDGF gene in the fibroblasts of wounds. Due to the oncogenic potential of the PDGF gene [Gazit, A.,. et al., 1984 *Cell* 39:89–97] such procedures require a strictly circumscribed expression of PDGF.

A major stumbling block to the use of growth factor therapy for the treatment of non-healing wounds has been the difficulty in protein delivery [Elia and Friend, 1975, *J. Cell Biol.*, 65:180–191; Chen and Okayama, 1989, *Mol. Cell. Biol.*, 922:2745–2752; D. Greenhalgh et al., 1990, *Am. J. Pathol.*, 136:1235–1246; T. Mustoe et al, 1994, *Arch. Sur2.*, 129:213–219; G. Hubner et al., 1995, *Cytokine*, 8:548–556]. All animal and clinical trials to date have thus far required large doses and repeat administration of growth factor in order to favorably influence wound healing (D. Greenhalgh et al., cited above, T Mustoe et al., cited above) Previously, methods including in vivo retroviral transfection, in vitro DNA transfection and autologous transplantation, plasmid DNA, and DNA-coated particle bombardment, have met with limited success because of poor gene transfer and limited biologic effect [Chen and Okayama, cited above; C. Andree et al., 1994, *Proc. Natl. Acad. Sci. USA*, 91: 21188–12192; G Kruegger et al., 1994, *J. Invest. Dermatol.*, 103: 76–84s; U. Hengge et al., 1995, *Nature Genet.*, 10:161–166; S. Benn et al., 1996, *J. Clin. Invest.*, 98:2894–2902; I. Ciernik et al., 1996, *Human Gene Ther.*, 7:893–899].

Thus, there remains a need in the art for methods and compositions useful in treating wounds, as well as in inducing cell growth, neovascularization and repair in injured or grafted mammalian, particularly human, tissue.

SUMMARY OF THE INVENTION

In one aspect, the present invention involves a method for increasing/inducing vascular development in mammalian tissue by delivering to the tissue a replication defective recombinant virus, preferably adenovirus, comprising a human growth factor gene under the control of regulatory sequences capable of directing expression of that gene in the tissue. The tissue can include the heart, arteries, veins or organs, such as kidney, liver, etc. In a selected embodiment, the tissue is human skin. This method enables the production of growth factors by different cells in the skin and/or in other tissue.

In another aspect, the invention provides a method for enhancing the repair of a wound in a mammal comprising administering to the mammal (preferably a human) a recombinant replication defective virus, preferably adenovirus, comprising a growth factor gene under operative control of regulatory sequences which direct the expression of said growth factor in the area of said wound. Expression of the growth factor thus enhances fibroblast growth and formation into a matrix, enhances keratinocyte growth and angiogenesis, and thus enhances wound closure.

Another aspect of this invention is a method for administering into poorly vascularized tissue (eg., skin) to be transplanted just prior to transplantation the virus containing the growth factor gene. Specifically, the genes desirably administered to a skin culture are $VEGF_{121}$ and PDGF-B.

In still another aspect, the invention provides a composition comprising tissue to be transplanted (e.g., human skin) which is infected with a recombinant virus which directs expression of VEGF or PDGF prior to transplantation.

In still another aspect, the invention provides a method of engrafting tissue onto a site of tissue injury in a mammal by (a) infecting a culture of human fibroblasts with about 10 pfu/cell of a recombinant replication defective virus, preferably adenovirus, comprising a selected growth factor gene under operative control of regulatory sequences which direct the expression of said gene product in said fibroblasts prior to transplantation; (b) placing said infected fibroblasts onto the site, and (c) placing tissue to be grafted at the site over the infected fibroblasts. The tissue (a) may also be treated with the virus.

In yet a further aspect, the invention provides a novel animal model for disease comprising an immunodeficient mouse, e.g., SCID or RAG mouse, stably engrafted with mammalian adult skin, preferably human skin, or other mature tissue infected with a recombinant virus which directs expression of VEGF or PDGF prior to engraftment.

In still a further aspect, the invention provides a method for screening angiostatic compounds useful in the treatment of pathological states such as VEGF-induced hemagiomas, particularly those resistant to conventional treatment, and other pathological states, such as cancers. This method comprises the steps of exposing the human skin graft on the animal model described above (in which the human tissue or at least a fibroblast layer was infected with a recombinant adenovirus expressing VEGF) with a test compound and observing the effect of the test compound on the process of formation and resolution of hemangiomas or growth of fibroblasts, keratinocytes, and/or angiogenesis in the graft. Compounds which reduced the process of hemangioma formation or enhanced the resolution thereof or enhanced cell grwoth and/or angiogenesis may be selected for the treatment of such hemangiomas in humans.

Other aspects and advantages of the present invention are described further in the following detailed description of the preferred embodiments thereof.

DETAILED DESCRIPTION OF THE INVENTION

Figure 1:
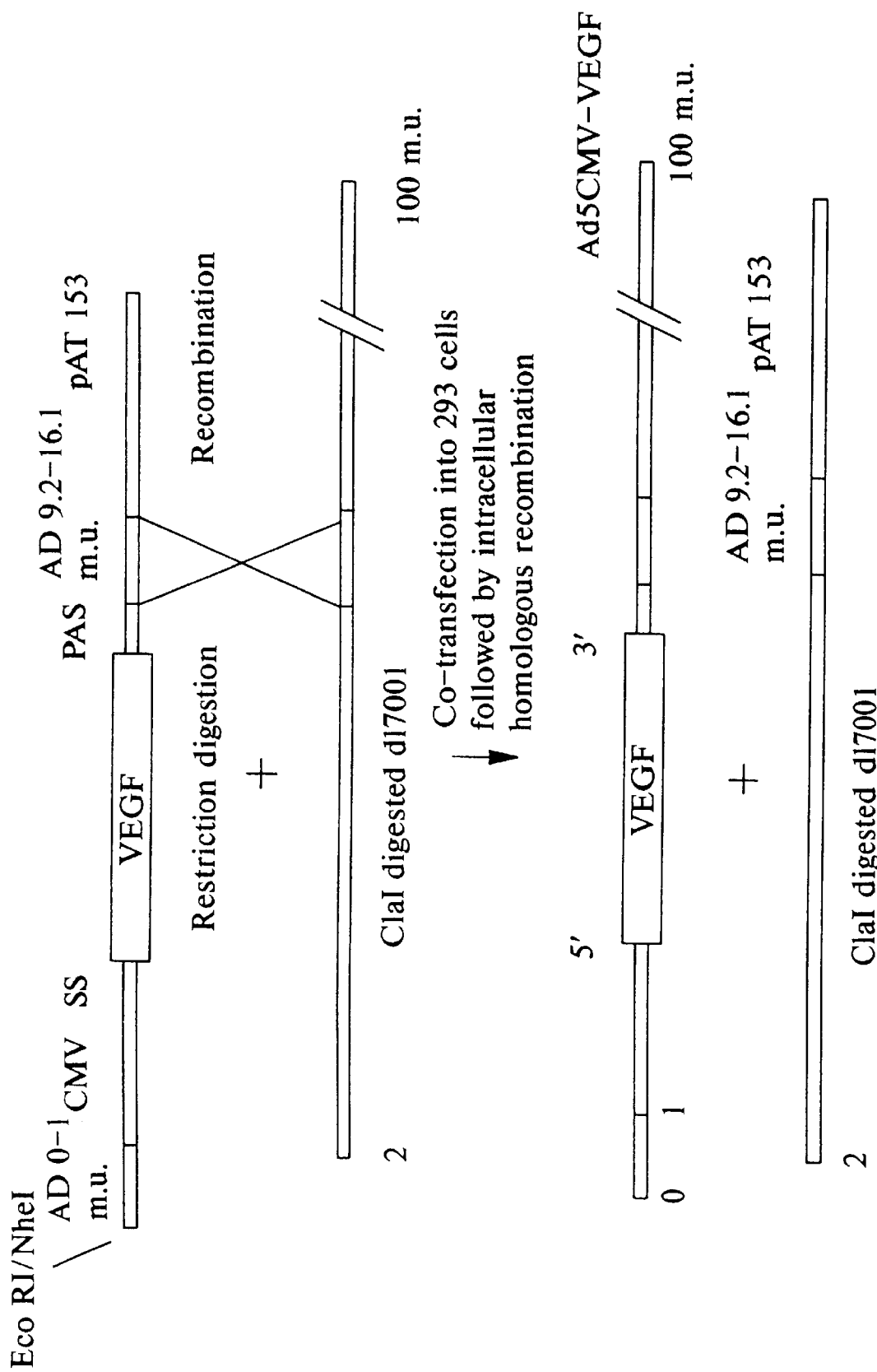
FIG. 1 is a flow chart illustrating the construction of $VEGF_{121}$ recombinant adenovirus.

The present invention provides methods and compositions for enhancing the healing or repair of defects in mammalian tissue, for example, wounds, particularly non-healing wounds, burns, and other tissue damage. In a preferred embodiment, the tissue to be treated by the method of this invention is human skin and cultures of human skin for grafting. However, this method is useful similarly with other mammalian tissue and organs, e.g., heart, kidney, liver, arteries, etc. The methods and compositions of the invention have proven effective in murine models of tissue re-vascularization, as well as in wound repair and closure.

I. Methods of the Invention

According to this invention a method is provided for inducing repair and neovascularization in mammalian tissue, specifically in skin which is damaged by a wound, injury, surgery, disease or aging. The method involves administering to such injured or defective tissue or wound in a mammalian subject a replication deficient virus carrying a selected growth factor gene. Infection of the tissue with the virus results in localized over expression of the selected growth factor at supraphysiologic levels, which induces growth of fibroblasts and keratinocytes, and neovascularization around the site of administration. The virus-mediated gene transfer for the induction of endogenous growth factor over expression augments inflammation and enhances wound healing. In addition, clearance of the transgene allows the augmented wound healing response to shift from the inflammatory to the remodeling phase during which a provisional wound matrix is deposited. This approach offers distinct advantages over other previous attempts at the delivery of recombinant DNA for the purpose of augmenting wound healing and re-vascularization of tissue.

A. Selected Growth Factors

Among the growth factors particularly useful in the present invention are vascular endothelial growth factors (VEGF) and platelet derived growth factor (PDGF), which are described in detail in the background above. Many variants, naturally occurring and synthetic, have been disclosed which are VEGFs and PDGFs. For use in the virus construct of this invention, the cDNA coding sequence of human $VEGF_{121}$ [E. Tischer et al, 1991, *J. Biol. Chem.*, 266:11947–11954 is employed; see also Genbank Accession Nos M63971–M63978]. $VEGF_{121}$ is a 121 amino acid protein, a functionally active dimer of 36 kDa, 32 kDa, and 28 kDa [Houck, K. A, 1991, *Mol. Endocrinol.* 5:1806–1814; Ferrara, N, et al, 1991, *Growth Factors,* 5:141–148], the result of homo- and heterodimeric associations of the monomeric 18 kDa glycosylated protein and the 14 kDa ungly-cosylated species. Of the four VEGF isoforms, only VEGF$_{121}$ lacks exon 7 and does not bind cell surface heparin, possibly explaining its proliferation-enhancing effect [Houch, K. A, et al, 1992, *J. Biol. Chem.* 267:26031–26037]. For use in the method of this invention VEGF$_{121}$ is preferred. Similarly for use in other mammalian species, mammalian VEGF$_{121}$ homolog sequences are preferably used.

For use in the virus construct of this invention, the human PDGF-B gene [T. Collins et al, 1985, *Nature,* 316:748–750, Genbank Accession Nos. MSSISA3-7, MSSIS1-5] is exemplified. Other useful PDGF genes include those described by L. Ratner et al, 1985, *Nature Acids Res.,* 13:5007–5018; and also the PDGF-A gene. Similarly for use in other mammalian species, mammalian PDGF homolog sequences are preferably used. It should be understood by one of skill in the art that other modifications of these growth factors may be used in the same manner as described herein.

B. Recombinant Virus

The functional requirements for the recombinant virus useful in the present invention are that it allows a burst of explosive production of the selected growth factor; that it infects target cells; that it carries the selected gene; and that it is replication defective. A number of viruses are known for use in delivering genes to heterologous tissue, such as vaccinia or other poxviruses and may be useful in this invention. Presently, a replication defective adenovirus is the preferred vector for permitting endogenous over expression of the selected growth factor gene products, such as VEGF or PDGF according to this invention. Adenoviruses as vectors are preferred for the method of this invention, because adenovirus is capable of infecting non-dividing cells or dividing cells. Adenoviruses infect all human skin cells including keratinocytes, fibroblasts, melanocytes and endothelial cells at more than 95% efficiency, making lengthy selection periods unnecessary [M. J. Bosma and A. M. Carol, 1991, *Ann. Rev. Immunol.,* 9:323–350; R. C. Mulligan, 1993, *Science,* 260:926–932; E. J. Kremer and M. Perricaudet, 1995, *Gene Ther.,* 2: 564–565]. Further, adenoviruses remain episomal and thus rarely integrate into the human genome [A. J. Bett et al, 1993, *J. Virol.,* 67:5911–5921]. The invention specifically provides recombinant replication-deficient adenoviruses containing the selected growth factor gene, which permit expression of the gene products in mammalian, preferably human, skin.

Another advantage of this invention, is that adenovirus-mediated gene expression in keratinocytes, melanocytes, endothelial cells, and fibroblasts remains stable in vitro for at least 2 to 6 weeks, depending on the proliferation rate of cells [K. Satyamoorthy et al, 1996, "*Utility of adenoviruses as gene expression modules in melanoma.*" In: (Maio M, ed) Proc. Int. Conf. Biol. Melanoma. IOS Press, Amsterdam, Netherlands; and Y. Setoguchi et al, 1994, *J.Invest. Dermatol.,* 102:415–421]. In contrast, soluble VEGF or VEGF delivered in another way, such as by lipid, for example, has a half-life of minutes to less than 12 hours.

To enhance growth factor gene expression in the present method, a replication defective adenovirus type 5 has been constructed with the E1 (the transforming region), and E3 gene regions (the immune modulatory region) or portions thereof deleted [Mulligan, cited above]. Replication-deficient Ad5 is safe for use in immunodeficient animals [Kiritsy and Lynch, cited above]. It has been used extensively as a gene-delivery system for therapies in experimental models of cancer [M. Feng el al, 1995, *Cancer Res.,* 55: 2024–2028; G. L. Clayman et al, 1995, *Cancer Res.,* 55:1–6; Z. Jin et al, 1995, *Cancer Res.,* 55:3250–3253; and L. Cordier et al, 1995, *Gene Ther.,* 2:16–21] and cardiovascular diseases. It has also been used for treating human gliomas and congenital diseases such as cystic fibrosis.

The exemplary recombinant virus used in this study is a modified adenovirus type 5, dl7001 strain which is characterized by a deletion in the E3 region [Ranheim, T. S., et al, 1993, *J. Virol.* 67:2159–2167]. DNA sequence analysis of the E3 region of this virus indicates deletion endpoints between nucleotide 594 and nucleotide 3662 in the E3 region, where nucleotide I corresponds to the EcoRI site of Ad5 at 27,331 bp. All E3 region open reading frames are deleted in dl7001. For use in this invention, the El gene region of dl7OOl is deleted rendering the virus replication defective. This recombinant virus is non-lytic and does not induce apparent phenotypic changes in infected skin cells.

However, the present invention is not limited to the dl7001 recombinant adenovirus. Other known replication defective adenoviruses and any new adenoviral vectors to be described are anticipated to be useful in the methods and compositions of this invention.

Similarly, this invention is not limited by the selection of the promoter useful in the recombinant virus, i.e., the native viral promoter is replaced using techniques known to those of skill in the art. Desirable promoters include the CMV promoter, the Rous sarcoma virus LTR promoter/enhancer, the SV40 promoter; the chicken cytoplasmic β-actin promoter [T. A. Kost et al, 1983, *Nucl. Acids Res.,* 11(23):8287]; the promoter for tyrosinase, which is a melanocyte-specific pigmentation gene [H. N. Antoniades et al., 1993, *Am. J. Pathol.,* 142: 1099–1110]; the promoter for keratin 5, which is specific for basal layer keratinocytes [G. Schultz et al, 1991, *J. Cell. Biol.,* 45:346–352; R. L. Brown et al, 1994, *J. Surg. Res.,* 56: 562–570], the promoter for flt-1, an endothelial cell-specific growth factor receptor [J. Gailit et al, 1994, *J.Invest. Dermatol.,* 103:221–227]; the promoter for Mel-CAM, a gene expressed by endothelial cells and melanoma cells and the mouse pro-alpha 1(1) promoter. Still other promoter/enhancer sequences known in the art, including naturally occurring viral promoters, may be readily selected by one of skill in the art.

In the recombinant virus, the sequence of the selected growth factor may be inserted under the control of the selected promoter in any region of the viral genome not essential for the formation of the recombinant virus. For example, in the embodiments described in the examples, growth factor cDNAs are inserted in place of the deleted E1 region of the replication defective adenovirus, and can only replicate in human embryonal kidney 293 cells available from the American Type Culture Collection under Accession No. CRL 1573 (which contain 11% of the viral genome including the E1 region). However, alternatively, the growth factor gene may be inserted into non-essential E3 or other regions. Such regions may be selected by one of skill in the art.

In a further embodiment, the recombinant virus may be constructed to contain tandem genes in place of the single selected gene as above described. For example, a gene construct containing VEGF$_{121}$ and PDGF-B (or with transforming growth factor-β) which is expressed by a single promoter can be used in place of the VEGF$_{121}$ gene under control of a promoter.

The recombinant viruses carrying single growth factor genes or tandem repeats of these genes can be prepared without resort to undue experimentation by one of skill in the art in view of the description herein and techniques of recombinant virus construction available in the art See, for example, the descriptions of the references cited above and other known art, such as International Patent Publication WO96/26285, published Aug. 29, 1996.

C. Performance of the In Vivo or Ex Vivo Methods of the Invention

Directed expression of such growth factors according to the method of this invention is useful in wound repair in mammalian tissue in a variety of situations. The present invention provides for endogenious over expression of a growth factor to provide optimal synthesis and secretion into the microenvironment for a longer lasting biological effect than is permitted by direct administration of the proteins themselves. According to one embodiment of the method of this invention, a recombinant adenovirus which can direct expression of a selected growth factor gene, e.g., $VEGF_{121}$, may be administered to the injured tissue. The recombinant virus bearing a gene encoding a VEGF or PDGF protein may be administered to a human or other mammalian patient, preferably suspended in a biologically compatible solution or pharmaceutically acceptable delivery vehicle. A suitable vehicle is sterile saline. Other aqueous and non-aqueous isotonic sterile injection solutions and aqueous and non-aqueous sterile suspensions known to be pharmaceutically acceptable carriers and well known to those of skill in the art may be employed for this purpose.

Conventional and pharmaceutically acceptable routes of administration include intramuscular, intracutaneous, intradermal, subcutaneous and other parental routes of administration. Routes of administration may be combined, if desired, or adjusted depending upon the extent and type of injury or the tissue being treated. Preferably the recombinant virus is injected intracutaneously or intradermally where the selected tissue is skin. One of skill in the art practicing this method may select appropriate routes.

The recombinant virus is administered in an "effective amount", that is, an amount of recombinant virus that is effective in a route of administration to transfect the selected tissue (e.g., skin) cells and provide sufficient levels of expression of the growth factor to provide a therapeutic benefit, i.e., enhance fibroblast and keratinocyte growth, enhance vascularization of the injured tissue. See, e.g., the amounts administered in the examples below. Doses or effective amounts of the recombinant replication defective virus will depend primarily on factors such as the tissue being treated, e.g., the type of skin damage being treated. The health of the subject mammal is not relevant due to the known safety of adenovirus use. For example, an effective amount or dose of a recombinant adenovirus according to this invention is generally in the range of from about 10 pi to about 1 ml of solution containing concentrations of from about $1 \times 10$ to $1 \times 10^{12}$ plaque forming units (pfu) virus/ml. A preferred dose is from about 50 to about 500 $\mu$l saline solution at the above concentrations. Most preferred for the treatment of skin is a dosage, administered intracutaneously, of about $5 \times 10^8$ recombinant virus particles per $cm^2$ of skin, based upon the size of the injury being treated.

In another embodiment of the method of this invention, the recombinant adenovirus carrying the selected growth factor gene is injected into a cell culture or other tissue intended for grafting or transplantation. A preferred example is the introduction of the growth factor-bearing adenovirus into fibroblasts. Preferably the recombinant virus is introduced into a cell culture at a concentration of about 10 pfu/cell in culture. The culture exposed to the recombinant virus is cultured for about 24 hours and then used for grafting or transplantation according to the methods described herein or in conjunction with conventional methods. Preferably, the adenovirus-containing fibroblasts are applied directly to the site of the wound, or the cells are embedded in a gel, e.g., Matrigel, for application to the wound site. Alternatively, the fibroblasts are grown on a membrane which dissolves in vivo. Thereafter, a graft of other (transplanted) tissue is placed over the fibroblast layer. The infected fibroblast layer overexpresses the growth factor for between about 10 to about 14 days. Introduction of such infused fibroblasts into a graft environment or a wound site enhances the cellular and vascular development both in and around the transplanted tissue and permits larger surface areas of skin or other tissue or thicker tissue to be transplanted successfully. Rapid vascularization and deposition of fibroblast matrices and keratinocytes occurs within days once the infected tissue (e.g., skin) is transplanted. Further, this method requires only a single administration of the recombinant virus. If the transplanted tissue which overlays the fibroblast layer is poorly vascularized or thick, the transplanted tissue itself may also be infected with a similar amount of the recombinant adenovirus. This provides an advance in maintaining the viability of transplanted tissue.

II. Compositions of the Invention

Another embodiment of the present invention is a composition useful in the transplantation or grafting of tissue in a mammalian patient which comprises a culture of human or mammalian cells, preferably fibroblasts, infected with a recombinant adenovirus according to this invention. Preferably the grafted tissue contains about $5 \times 10^8$ recombinant virus particles per $Cm^2$ of cells in culture. This composition is prepared utilizing the method of this invention, and may be prepared within 24 hours prior to grafting or transplantation procedure. Such infused fibroblasts may be grafted onto a site of a wound or other tissue injury. Such infused fibroblasts may be employed to underlie another grafted tissue on the site of the injury as described above.

As still another embodiment of the present invention are other tissues, such as breast tissue, liver tissue, etc., which are similarly infected in vitro with the recombinant viruses of this invention and used for transplantation or grafting within 24 hours. The tissue is cultured iEi vitro in the same manner as the skin culture.

The method of this invention, which permits infection of these tissue cultures, permits larger surface areas of tissue or skin to be transplanted than when prepared by presently available methods. The tissue cultures prepared according to this invention revascularize more rapidly than cultures prepared in other known ways.

III. Animal Transplantation Model and Method of Preparation

The invention also provides a novel murine tissue transplantation model in immunodeficient mice which mimics the behavior of human skin or other mature mammalian tissue At present only very thin layers of skin or small fragments of other human tissues, generally 1–2 $mm^2$ can be grafted onto animals for experimental use. Such tissue, whether skin or other tissue, must be trimmed down prior to any engrafting. In contrast, this novel murine model allows experimental conditions closely mimicking those in human patients, and allows the use of full thickness of mature skin or other mature tissue Thus, this model provides a new molecular tool useful in studies of skin disease pathogenesis, skin disease therapy, reconstructive surgery of other tissue and tumor progression, and in assays for testing or screening therapeutically useful compounds for treatment of angio (lenic disorders, such as treatment-resistant hemangiomas, among others.

According to this invention, the murine model is a severe combined immunodeficiency (SCID) mouse, such as described in P. W. Soballe el al, 1996, *Cancer Res.*, 56:757–764 or a RAG1 [E. Atillasoy, 1997, *J. Invest.*

*Dermatol.,* 109:704–709] mouse, onto which is grafted a large fragment of full thickness human skin, or mature tissue, such as breast tissue, liver tissue, cartilage, etc. prepared prior to grafting by infecting the tissue with the recombinant adenovirus as described above. This graft may overlay the infected fibroblast layer as above-described. Preferably, the recombinant adenovirus employed carries the gene for $VEGF_{121}$, or PDGF-B, or tandem versions of such growth factor genes. This model is described in more detail in Example 2.

Once grafted onto the mice by conventional means, the infected tissue cells express the selected growth factors which induce rapid neovascularization by the mouse vessels, which allow survival and growth of the mature tissue. This model permits the engraftment and study of large tissue areas, including mature skin and mature untrimmed tissue. This model provides an effective method for successful skin grafting of tissues that previously were too thick for obtaining viable skin grafts.

IV. Utilities of the Methods and Compositions of this Invention.

The compositions and methods of this invention have utility in both research and drug development, as well as in wound treatment and surgery, such as plastic surgery or transplantation, and in the treatment of angiogenic disorders. The present invention permits individual growth factors to be delivered at supraphysiologic levels, in order to better modify scar tissue, wound healing, and enhance tissue generation in problem wounds. The compositions and methods permit one to enhance healing of wounds in an impaired environment, and modify or reduce scarring in patients with abnormal scarring. The present invention may be useful to enhance a local wound to allow simple closure, either through skin grafting, or endogenous healing. The present invention helps achieve closure of difficult wounds. The method of delivering the adenovirus carrying the selected growth factor to the site of the tissue injury is also useful during reconstructive surgery for collateral tissue vascularization by inducing hypervascularization.

According to the methods of this invention, large surface areas of tissue may be maintained in a viable state, and then used to close a wound or other tissue defects in surgical procedures. The model and the method of this invention may allow viable tissue healing in areas that would previously not be receptive towards healed tissue. The method and compositions of this invention provide the ability to successfully generate new tissue and preserve the viability of impaired tissues in the treatment of traumatically injured tissues or preserving surgically impaired tissues. For example, new extra tissue could be generated as described above prior to transfer, or the blood flow and tissue development enhanced in existing tissue that would be required for successful transfer into a poorly vascularized 'random area' of tissue or tissue absence. Frequently poorly vascularized areas of tissue, such as transplanted tissues utilized to cover up traumatic wounds, or wounds that are created after the surgical resection of cancer, or potentially wounds that have developed due to ischemic conditions, necrose when transferred into a new location. The present invention may enhance the viability of the random area of tissue, either through improving its vascular supply or the development of more functional tissue.

Another use of the methods and compositions of this invention is in the treatment of ischemic ulcers or macular degeneration due to peripheral vascular disease, diabetes, aging and radiation necrosis. Currently, the standards of treatment require prolonged dressing changes, continuous surgical debridement, and ultimately the surgical transfer of tissues, either through local flaps or microvascular free tissue transfers. These transfers require taking healthy tissue from one area of the body and donating it to the impaired recipient site.

The present invention also finds use in enhancing microvascular tissue transfer, breast reconstruction in surgically created wounds and radiation created wounds, as well as craniofacial surgery with regards to scar formation around various prosthetic implants, onlay bone graft healing, as well as tissue preservation and improving free tissue transfer survival.

There are also numerous research uses for the compositions of this invention, for example, for studying the events that occur after the injection of growth factors, such as PDGF, VEGF, TGF-P and insulin-like growth factor, or others, on the modification of scar tissue, such as keloid scarring. Elevated incidence of VEGF in the periphery of keloids accounts for the abundance of tissue growing in the periphery and the relative avascular central fibrotic characteristics within the keloid dermis. The ability to maintain the viability of human keloids on the SCID mouse utilizing VEGF and PDGF serves as an interesting model to study the behavior of keloids.

Further, the model and methods of this invention will permit evaluation of the effectiveness of delivering supraphysiologic levels of various growth factors in other impaired wound healing models, such as closure of the acutely ischemic, chronically ischemic, and radiated wounds.

The animal model which bears engrafted human skin infused with an adenovirus and/or an underlying Ad-infected fibroblast layer which permits expression of VEGF (or PDGF) is also useful in a method for screening compounds for the treatment of angiogenic disorders. As one example, described in detail below, the VEGF treated skin grafts produce a result which mimics the development and resolution of hemangiomas. Hemangiomas may, under some circumstances, be life-threatening and current therapies use corticosteroids [Folkman, J. 1995, *N. Engl J. Med* 333: 1757–1763] or IFNα-2a [Ezekowitz, R. A et al, 1992, *N. Engl. J. Med.* 326: 1456–1463], the latter compound down regulates the production of fibroblast growth factors [Singh, R. K. et al, 1995, *Proc Natl. Acad. Sci. USA,* 92:4562–4566] There is presently no treatment for those hemangiomas which do not respond to IFNα-2a. In the proliferating stage, hemangiomas have been shown to express VEGF [Cohen, T. et al, 1996, *J. Biol. Chem.,* 271:736–741; Uchida, K. et al, 1997, *Urology,* 49:285–286].

Thus, the animal model of this invention in which the graft develops hemangioma-like lesions in human skin provides an assay for the screening of factors controlling the proliferation and involution of such lesions. Such a method is performed by contacting the VEGF-infused graft with a test compound, and determining the effect of the test compound on the progression of the hemangioma development and involution. Test compounds which promote involution or repress the normal hemangioma development observed in this model as detailed in the examples would be selected candidates for therapeutic use.

This invention also provides an assay which permits the development and testing of angiostatic compounds for the clinical management of other pathological states, such as cancers. For example, the invention provides a method for studying angiogenesis or for screening a test compound for use in tissue repair or tissue vascularization which includes the steps of (a) providing an immunodeficient mouse carrying an engrafted mammalian tissue, said tissue infected with about 10 pfu/cell of a recombinant replication defective virus, said virus comprising a selected growth factor gene under operative control of regulatory sequences which direct the expression of said growth factor in said tissue prior to engraftment onto said mouse, (b) contacting the engrafted tissue with a test compound; (c) observing the effect of the compound on growth of fibroblasts and keratinocytes and angiogenesis in said engrafted tissue; and (d) comparing the effects of step (c) to the engrafted tissue without the test compound. Such an assay may employ conventional assay reagents, and is within the skill of the art given the teachings of this invention.

The following examples illustrate the components and method of this invention, and do not limit the scope of the present invention, which is embodied in the appended claims.

EXAMPLE 1

Construction of AD/VEGF and AD/PDGF

A. Ad/VEGF

A replication-deficient adenovirus type 5 (AdS) containing $VEGF_{121}$ cDNA (Ad/VEGF) was generated as follows usin(g conventional techniques. See also, the flow chart of FIG. 1.

The $VEGF_{121}$ gene [E. Tischer et al, 1991, *J. Biol. Chem.*, 266:11947–11954; see also Genbank Accession Nos M63971–M63978] previously amplified by reverse transcription-PCR and cloned into the SmaI site of pbluescript II SK+(Strategene, LaJolla, Calif.), was subcioned into the EcoRI/XbaI site of a NotI-modified pSL301 vector (Gene Therapy, Vector Core, University of Pennsylvania/ The Wistar Institute). The resulting plasmid was cut with NotI, subcloned into the NotI site of the adenoviral vector pAdCMV (Gene Therapy Vector Core, University of Pennsylvania), and cut with EcoRI to determine the orientation of the VEGF gene. The resulting expression plasmid contains: 5'-0 to 1 adenovirus type 5 map units (containing an inverted terminal repeat (1TR) and packaging signals), a cytomegalovirus intermediate early (CMV) promoter and SV40 polyadenylation sequences (PAS), the $VEGF_{121}$ gene flanked at the 3' end by map units ~9.6 to 16 of adenovirus type 5 sequence, the remainder of the plasmid being that of a pUC derived plasmid. Such plasmids and the techniques for generating them to contain other genes are described in the art [see, e.g., K. Kozarsky et al, 1994, *J. Biol. Chem.*, 269:13695–13702, X. Ye et al, 1996, *J. Biol. Chem.*, 271:3639–3646; and Mulligan, cited above].

DNA of dL7001 AdS lacking the E1 and E3 genes [Ranheim, T. S., et al, 1993, *J. Virol.* 67:2159–2167] was cut with ClaI to remove map units 0–2 according to procedures described in Mulligan, 1993, cited above, and calcium phosphate precipitated together with 10 µg of NheI-digested pAdCMV containing the VEGF gene in the sense orientation. This DNA was transfected into human embryonic kidney 293 cells [American Type Culture Collection] which contain the E1 gene of Ad5. Cells were incubated with vectors in serum-free medium for 2 hours and serum was added to a final concentration of 10%. After 5 hours, 293 cells were subjected to a 10% glycerol shock for 2 minutes in serum-free DMEM. Cells were grown overnight in DMEM with 10% FCS and overlayed with 0.8% agar (DIFCO, Detroit, Mich.) in Eagle medium (GIBCO/BRL, Grand Island, N.Y.) supplemented with 2%/o FCS and 0.5 mM $MgCl_2$. Fresh overlay was added every 4 days until individual plaques appeared, typically by day 16.

Intracellular homologous recombination occurs in the growing cells as depicted in FIG. 1 and the resulting plaques indicate the development of a recombinant viruses containing map units 0–1 of Ad5, followed by the cassette sequence containing VEGF and its regulatory sequences, flanked by adenovirus sequences from map units 9.2 to 100 (with the dl17001 E3 deletion) [A. J. Bett et al, 1993, *J. Virol.*, 67:5911–5921]. Plaques were expanded in 293 cells grown in 35-mm dishes and fresh medium as added every other day until the appearance of cytopathic effects. Cells were then harvested and adenoviral DNA was isolated.

The DNA was cut with BarnHI, electrophoresed on a 1% agarose gel and analyzed by Southern blotting using the EcoRI/XbaI fragment of the VEGF gene as the template for random priming using [$^{32}P$] dATP to select positive plaques. After two additional rounds of plaque purification to eliminate contaminating viruses that do not contain the VEGF gene, and Southern blot analysis, a single plaque was selected to obtain a large preparation of recombinant adenovirus using 50×150 $cm^2$ tissue culture plates. The resulting recombinant virus, Ad/VEGF, was purified by cesium chloride gradient centrifugation and titrated as plaque-forming units (pfti) on 293 cells overlayed with agar. This plasmid is used in subsequent examples.

B. Ad/PDGF

Ad/PDGF was constructed by analogous procedures as described for VEGF, except that the PDGF-B gene [T. Collins el al, 1985, *Nature*, 316:748–750, Genbank Accession Nos. MSSISA3-7, MSSIS1-5] was the foreign gene. See, FIG. 2.

A 1.2 Kbp Pst I/Eco RI cDNA fragment encoding the entire open reading frame of the full length PDGF-B cDNA (Dr B. Westermark, University Hospital, Uppsala, Sweden) was sub-cloned into the Pst I/Eco RI digested, Not I modified plasmid pSL301 (Invitrogen, Carlsbad, Calif., Vector Core, University of Pennsylvania). The resulting plasmid was cut with NotI (Promega, Madison, Wis.) and the fragment subcloned into the NotI restriction site of the adenoviral vector pAdCMV-Link. 1 [K. Kozarsky et al, 1993, *Somat. Cell. Mol. Genet.*, 19:449–458]. The resulting plasmid was cut with EcoRI (Promega) to determine the orientation of the PDGF-B gene and a clone with the PDGF-B gene in the sense orientation, pAdCMV, was selected for use in the co-transfection assay.

pAdCMV was cut with NheI (Promega) and co-transfected into human 293 cells along with ClaI digested dL7001 adenoviral genome lacking the E1 and E3 genes [T. S. Ranheim et al, cited above] via calcium phosphate precipitation [Rosenfeld, M. A. et al, 1991, *Science*, 252:431–434]. After 2 hours incubation in serum-free DMNEM, 10% FCS (Sigma Chemical Co., St. Louis, Mo.) was added to the cells. After a further 4–5 hours, the cells were subjected to a 10% glycerol shock for 2 minutes in serum free DMEM and then grown overnight in DMEM with 10% FCS. After this time cells received a 0.8% agar (DIFCO Labs, Detroit, Mich.) overlay of basal Eagle media (GIBCO/BRL), supplemented with 2% FCS, 0.5 MM $MgCl_2$ and antibiotics. Fresh overlay was added every 4 days until the appearance of well defined and isolated plaques (typically around 16 days).

Plaques were expanded in 293 cells grown in DMEM containing 10% FCS with fresh media added every other day until cytopathic effects were observed. Cells were then harvested and putative adenoviral DNA isolated as previously described [B. Hirt, 1967, *J. Mol. Biol.*, 26:365–369]. The isolated DNA was digested with Bam HI (Promega) and the presence of the PDGF-B gene confirmed by 1% agarose gel electrophoresis, followed by Southern blot analysis using the PstI/EcoRI fragment of the PDGF-B gene as a probe. Positive plaques were further cloned by limiting dilution and again identified through Southern blotting. Recombinant adenovirus Ad/PDGF (PDGF-B/Ad5 or AdCMV-PDGF-B) containing the PDGF-B gene was assessed for protein production by Western blotting. Ad/PDGF virus was expanded on 100 150 cm² tissue culture plates and purified twice over cesium chloride step gradients using ultracentrifugation. The final plaque-forming units (PFU) of the virus was determined by titration on 293 cells under an agar overlay [F. L. Graham et al, 1973, *Virol.,* 52:456–467]. The viral band was dialyzed against PBS and glycerol was added to 10% and stock virus (typically $2\times10^{10}$ plaque forming units (pfu)/ml) was kept at $-80°$ C. until use.

C. AdLacZ

AdLacZ (also Ad/LacZ or Ad-CMV-LacZ) was obtained from (The Institute for Human Gene Therapy, Vector Core, University of Pennsylvania). It is an E1/E3-deleted recombinant virus producing the β-galactosidase protein under the control of the immediate early cytomegalovirus promoter, and is used throughout these examples as a control. This virus was purified by cesium chloride centrifugation and the final plaque-forming units (PFU) were determined by titration on 293 cells under an agar overlay [F. L. Graham et al, cited above].

EXAMPLE 2

Human Skin/Mouse Chimeric Model of the Effects of AD/VEGF on Normal Human Skin

This experiment demonstrates that the Ad/VEGF vector of Example 1 transduces the VEGF gene to all skin cells at high efficiency and induces a strong increase in human blood vessel formation when injected into normal human skin grafted to immunodeficient SCID or RAG-1 mice.

Human skin has a very unique architecture which differs from murine skin in both epidermal and dermal structures. Normal human skin can be maintained alive and functional when transplanted to animals that are unable to reject these grafts. The severe combined immunodeficiency disease (SCID) mouse lacks a T cell response and has only an abortive B cell response. Grafted, full-thickness human skin remains histologically intact with minimal infiltration of murine mesenchymal cells. In addition, human or mouse inflammatory cells are free to migrate into the grafts. The human vasculature remains intact by anastomosing with mouse vessels, and human blood vessels can be induced to sprout and infiltrate secondary grafts such as human or mouse tumors After wounding, human skin grafts show the same patterns of expression of adhesion receptors and extracellular matrix proteins as skin after wounding in patients.

Thus, the human skin/mouse chimera model is superbly suited to investigate systematically the pathogenesis of defined skin diseases such as melanoma or of wound healing as a first step in developing new strategies for therapy.

A. Grafting of Human Skin.

One to two cm² of full-thickness human skin is grafted into a circular graft bed of the back of mice, from which the mouse skin is removed down to the fascia [P. W. Soballe et al, cited above]. Foreskin (approximately 80% of total) or adult skin (blepharoplasty) is used for human donor skin. The skin is grafted within 24 to 48 hours after surgery. Skin is sutured in place, and only mice with completely healed grafts are included in the experiments, generally after 3 to 4 weeks. The take rate for grafting of full-thickness human skin is approximately 85% on nude mice and over 95% on SCID or RAG-1 mice.

The histological appearance of the human skin is normal, including preservation of the epidermal structures (stratum corneum, stratum granulosum, stratum spinosum, stratum basalis, and rete ridge pattern), The dermis shows intact superficial and deep microvascular plexuses. The papillary and reticular dermal collagen appears normal with normal spindle cell (fibroblast) activity (not hyper- or hypocellular). The human nature of the cells in the grafts was confirmed immunohistologically using antibodies specific for human endothelial cells, fibroblasts, keratinocytes, and melanocytes. Mast cells (identified by anti-chymase antibodies), Langerhans cells (identified by anti-CD 1a antibodies) persist in the skin for at least 6 weeks, melanocytes for the life time of the graft. Additional markers used for confirmation of the human nature of the cells in the grafts were human-specific alu sequences stained by iii situ hybridization and the characteristic nuclear staining with Hoechst dye with readily distinguishes murine from human nuclei.

B. Gene Transduction.

Based on experiments with recombinant adenovirus containing the β-galactosidase (LacZ) reporter gene (Ad/LacZ), between about $10^8$ to $10^{11}$ Ad/VEGF pfu/per injection of 100 μl is used into the human skin. In large grafts of 2 cm², growth and control viruses are injected into the same graft in opposite areas. Smaller grafts are injected with one recombinant virus to avoid potential cross-contamination of the two viruses. Each virus is administered at $10^8$, $10^9$, $10^{10}$, $10^{11}$, and $10^{12}$ pfu/dose.

The animals are sacrificed at each biopsy time point unless the subject mouse is maintained for continued observation. Biopsies are taken on days 1, 2, 4, 7, 14, 21, 28, 35, 60, and 90. An identical sample of the biopsy is frozen for immunohistological and in situ hybridization or fixed in formalin and embedded in paraffin for morphological analyses. These preliminary experiments determine the optimal viral dose for transduction of dermal cells.

In one experiment, thin human skin was grafted onto the dorsal surface of 24 SCID mice within 48 hours of excision. Thirty days postoperatively, human skin survival was confirmed and 100 μl of either saline or adenovirus suspension ($5\times10^8$ PFU) containing PDGF-BB, VEGF, or LacZ (control) was injected intradermally (n=6 per group). The animals were sacrificed at days 3, 7, 14, 21, 28, and 35 and gross observations were recorded at each time point prior to sacrifice. Skin samples were obtained for standard histology and immunohistochemical staining.

The gross appearance of Ad/VEGF infected grafts showed diffuse, raised, vascular lesions with a "hemangioma-like" appearance as early as 36 hours post injection. Representative samples demonstrated a ten fold increase in size at 3 days post-injection which plateaued at 7 days and remained for the duration of the study. Histologic evaluation of VEGF specimens revealed extensive proliferation of human and mouse endothelial cells, human fibroblast proliferation, and profuse neoangiogenic changes.

Grafts infected with Ad/PDGF-B revealed significant soft tissue growth, but with a less erythematous appearance. Histologic evaluation confirmed these findings, revealing profuse human fibroblast proliferation and moderate endothelial cell proliferation. Collagen analysis yielded predominately types I and III The gross and histologic soft tissue changes observed in the PDGF group resembled proliferative scar tissue. Both groups showed epidermal thickening with exaggeration of the rete ridges.

Results with Ad/VEGF in vivo demonstrate a strong cellular response: $5\times10^8$ pfu (plaque forming units) induce after intradermal injection a vascular response that becomes clinically visible after 2 to 3 days and persists longer than 49 days, when these initial experiments where terminated. The "hemangioma-like" lesion remained localized to the injection site. Control virus (Ad/LacZ) did not induce any swelling and redness. Histologically, Ad/VEGF-injected human skin showed increased blood vessel formation and some edema. The edema subsided after 2 weeks whereas the newly formed blood vessels persisted.

The method of this invention utilizing recombinant adenovirus carrying VEGF significantly increases the growth of human soft tissue and has a role in accelerated wound healing, tumor modification, and scar tissue manipulation.

EXAMPLE 3
Immunohistological and Histochemical Experiments

Immunohistological and histochemical experiments confirmed the human nature of the newly formed blood vessels described in Example 2. Hematoxilin-eosin staining of sections of human skin injected with $5 \times 10^8$ pfu Ad/VEGF from biopsies was performed 3 days, 14 days and 28 days after VEGF transduction with Ad/VEGF. Sections of human skin grafted to SCID mice, 3 days after injection with Ad/VEGF were also stained with MAb against human B3 integrin subunit, or with MAb against human PECAM-1, or with MAb against human MelCAM. Sections of human skin were also stained with Hoechst dye. Staining of sections with Hoechst dye indicates the typical nuclear pattern for human cells with individual mouse cells present. Staining of the same human graft was also done with anti-murine PECAM-1. Murine blood vessels were stained with anti-murine PECAMi 13 days after subcutaneous injection of Ad/rEGF.

Endothelial cells in the sections were reactive with human-specific monoclonal antibodies (MAb) defining B3 integrin subunit, PECAM-1, and Mel-CAM. MAb specific for mouse PECAM- I stained only occasional endothelial cells. The staining pattern of nuclei with Hoechst dye also confirmed the human origin of the cells. Injection of Ad/VEGF, on the other hand, subcutaneously into non-grafted mice induced a strong murine vascular response confirming that VEGF in skin cells transduced by Ad/VEGF also activated murine receptors.

An alternative assay for gene expression is the detection of mRNA by in situ hybridization. This assay is useful if cells secreting VE(C1 or an other growth factor are difficult to identify histologically. Biotinylated 18-mer (specific for the growth factor DNA or human alu sequences) is applied to formalin-fixed, paraffin-embedded tissue sections. Staining is done with streptavidin-horseradish peroxidase and stable diaminobenzidine, and counterstained with aqueous hematoxilin.

EXAMPLE 4
Western Blots

Figure 2A:
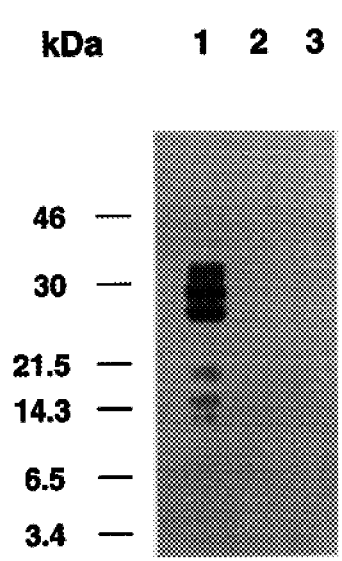
FIG. 2A is a Western blot of non-reduced supernatants 72 hours after viral transduction with WM-239A melanoma cells, usin,, a monoclonal antibody (mAb) specific for VEGF. Lane 1 is a WM-239A supernatant containing $AdVEGF_{121}$, lane 2 is a WM-239A supernatant containing a adenovirus vector carrying a β-galactosidase marker gene; lane 3 is a WM-239A mock-transfected supernatant. Blot e represents mature human $VEGF_{121}$, blot d represents an immature form of the growth factor. Blots a through c represent dimerized forms, with a representing the dimer of the immature form (d), b representing a dimer of (d) and (e) and c representing a dimer of mature $VEGF_{121}$.

In in vitro experiments, Ad/VEGF infection of human fibroblasts and biologically early human melanoma cells transduces the VEGF gene and induces synthesis and secretion. WM-239A melanoma cells were transduced with Ad/VEGF, an adenovirus vector carrying a β-galactosidase marker gene (Ad/LacZ) or mock transfected. A Western blot of non-reduced supernatants from these cells using a monoclonal antibody (mAb) specific for VEGF is shown in FIG. 2A. The mature $VEGF_{121}$, immature forms and various dimeric forms were identified.

Figure 2B:
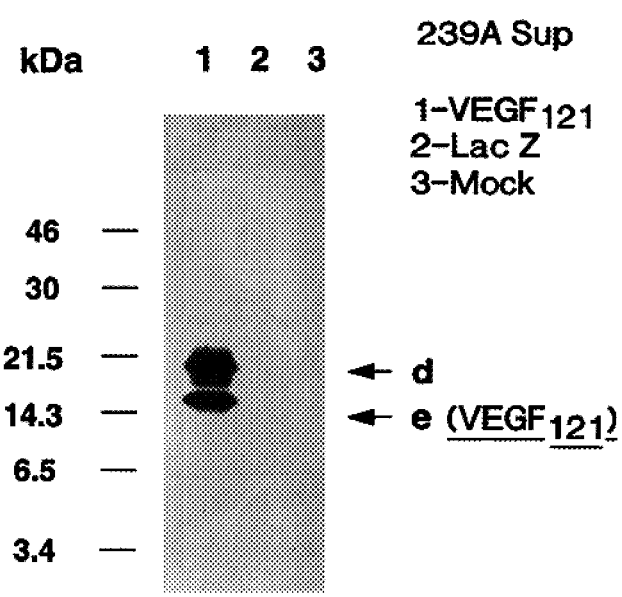
FIG. 2B is a Western blot of the supernatants of FIG. 2A, but reduced. The lanes are the same as described for FIG. 2A. The blot labeled e in lane 1 is $VEGF_{121}$ The blot labeled d is immature or glycosylated VEGF.
Figure 3:
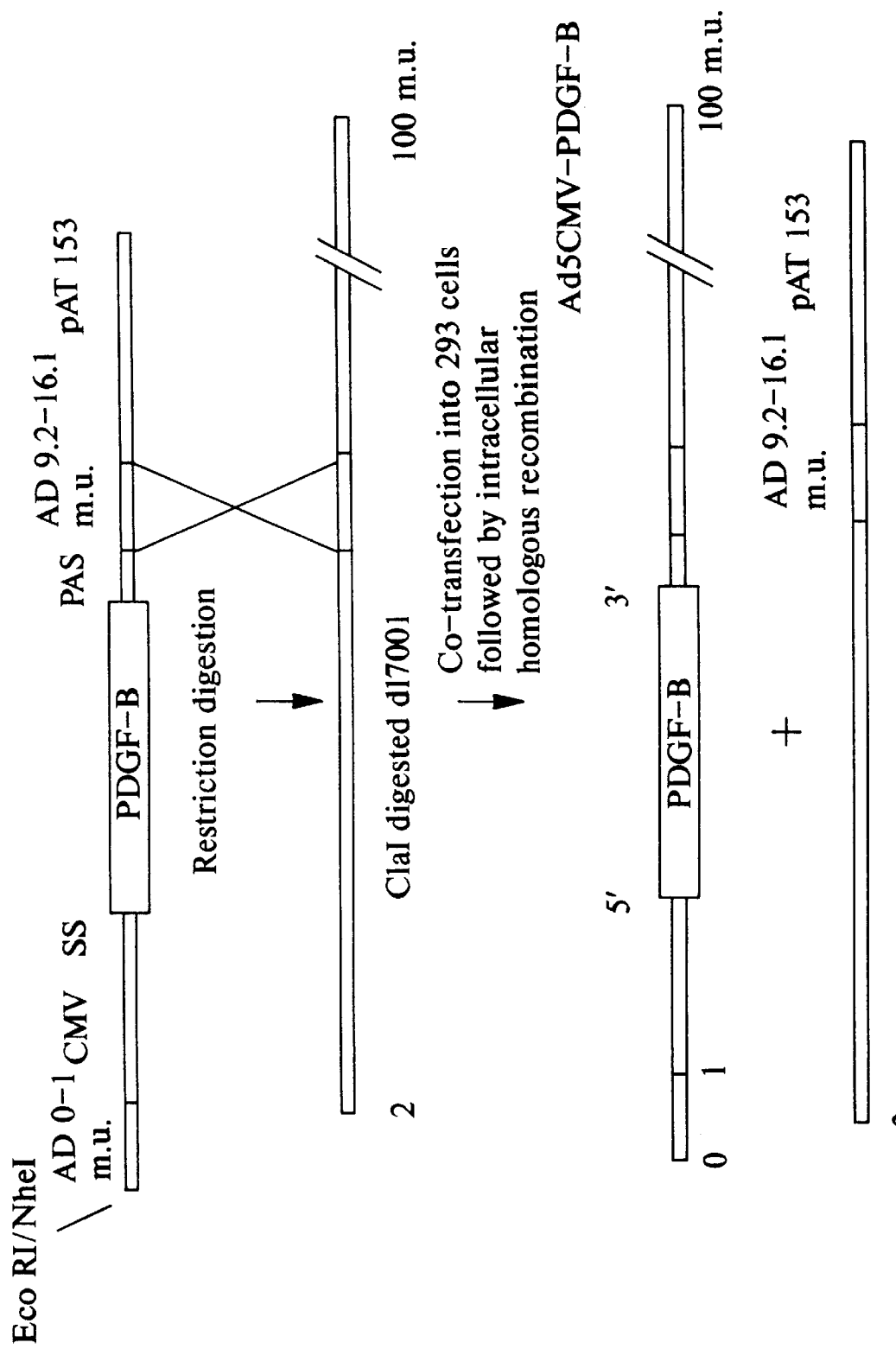
FIG. 3 is a flow chart illustrating the construction of PDGF-B recombinant adenovirus.

After the same supernatants were subjected to reducing conditions, the Western blot of FIG. 2B showed the mature and immature forms of $VEGF_{121}$. The secretion rate of VEGF 48 hours after transduction of 293 cells at 10 m.o.i. (multiplicity of infection) was between 5 and 8 pg/ml.

EXAMPLE 5
Characterization of Cellular Responses

The cell types that comprises the skin after VEGF over expression are identified using standard histological criteria and immunohistology for detailed identification (see Table 1) For identification of fibroblasts, antibody 451 (Table I) was developed. Balb-c mice were immunized, prior to fusion with P3X63Ag8.sp2/0 myeloma cells, with normal human fetal fibroblasts. The resulting hybridoma secretes an $IgG_1$ kappa antibody, which binds fibroblasts, and does not crossreact with other cells in the skin.

Table 1 lists other monoclonal antibodies (mAb) that specifically identify skin cells such as keratinocytes (GA733), endothelial cells (Mel-CAM, PECAM-1 [CD-3 1]), β3 subunit of monocytes/granulocytes (Lewis X or NCA), or monocytes (CD11c).

TABLE 1

Identification of human skin cells and mouse macrophages with MAb

| Cell Type | Antigen | Antibody | Isotype |
|---|---|---|---|
| Fibroblasts | 451 | 451 | IgG1 |
| Keratinocytes | GA733 | GA733 | IgG2a |
| Endothelial | Mel-CAM | A32 | IgG1 |
|  | PECAM-1 (human) |  | IgG1 |
|  | PECAM-1 (murine) |  | IgG1 |
|  | β3 integrin | SAP | IgG1 |
|  | avβ3 | Nu4B | IgG2a |
|  | PAL-E(lymph) |  | IgG1 |
| Melanocytes | gp75 | TA99 | IgG2a |
| Granulocytes | Lewis X | 29-1 | IgM |
|  | NCA | 20–32 | IgG2a |
| Monocytes (human) | CD11c | anti-Leu-M5 | IgG (Coulter) |
| Macrophages (mouse) | CD11b | M1/70.15 | IgG (ATCC TTB128) |
| Langerhans cells | CD1b | 4A76 | IgG2a (Biosource Inc.) |
|  | HLA-DR | 13–17 | IgG1 |

EXAMPLE 6
Role of VEGF in Wound Healing.

Vascularization is an important component of ring wound healing and tissue remodeling. The human skin graft model is superbly suited for wound healing analysis.

The wounds are 4 to 6 mm mid-reticular to papillary dermis wounds (partial thickness). The wounds are infected i) 15 minutes after hemostasis when inflammatory cells have not yet migrated into the wound region; ii) 6 hours later when inflammatory cells are expected to be present in the wound region and begin producing growth factors; and iii) 24 to 48 hours later when a granulation response has been initiated and fibroblasts have begun migrating into the wound area. Virus infection is accomplished by immersing the virus (Ad/VEGF or control preparation Ad/LacZ) into wound the and intradermal injection with a 30 gauge needle. The wounds are covered with a non-adherent petroleum gauze, then with Tegaderm® for 2 days only. Biopsies are taken on days 2, 4, and 7 after wounding.

EXAMPLE 7
Ad/VEGF Infection of Fibroblasts

A. Preparation of Fibroblasts:

DMEM (GIBCO/RL, Grand Island, N.Y.) supplemented with 10% FCS (Irvine Scientific, Irvine, Calif.) was used for culture of human dermal fibroblasts (FF302 or FF2209). FF302 fibroblasts were grown to 90% confluence and then washed and subsequently resuspended in 0% DMEM. AdVEGF ($5 \times 10^9$ PFU/ml; Example 1), AdLacZ ($5 \times 10^9$ PFU/ml; Example 1), or equivalent amounts of media was added to the cells at a multiplicity of infection (MOI) of 20:1, and fibroblasts were incubated for 2 hours. The cells were then washed, resuspended in 0% DMEM, and incubated for 24 hours. After this time, cells were collected and placed into a cold liquid mixture of 10% DMEM and Matrigel (100 μgs Matrigel/1.0 cc DMEM).

B. Western Blot Analysis

FF302 human fibroblasts were washed, resuspended in serum-free (0%) DMEM, and then infected with adenoviral construct or an equal amount of saline for 2 hours. Following this incubation, cells were washed and resuspended in DNIM 0%. Serum-free supernatant was collected after 72 hours and 50 μL was heated to 100° C. for 10 minutes in an equivalent amount of SDS sample buffer (10% SDS, 100 mM Tris [pH 6.8], 1% glycerol, 125 mg/ml bromophenol blue, 5% [v/v] 2-mercaptoethanol [12.5 M]), and run on a 15% polyacrylamide el. The gel was electroblotted to a PVDF membrane (Millipore Corp., Bedford, Mass.) overnight at 40 V and then blocked for 2 hours with 2% BSA in PBS containing 0.05%/o Tween 20. The membrane was then incubated at RT first with rabbit anti-human monoclonal antibody to recombinant VEGF (Ab3; R&D Systems) at a dilution of 200:1 and then with mouse antirabbit IgG labeled with alkaline phosphatase (Jackson Immuno Research Laboratories Inc., West Grove, Pa.) for 2 hours each. Following thorough washing of the membrane, visualization of bands was accomplished by incubation in 5-bromo-4-chloro-3-indolyl phosphate and nitroblue tetrazolium (Sigma, St. Louis, Mo.) as chromogen and substrate, respectively.

C. Results

Over expression of AdVEGF by cultured FF caused no significant autocrine cell growth increase over that of controls. Upon Western blot analysis, AdVEGF-infected FF expressed predominate bands at approximately 14 kD and 18 kD under reduced conditions, consistent with VEGF protein production in its reduced form. A positive control cell line (WM239A) which is known to heavily express VEGF protein upon infection with AdVEGF was used for comparison. Infection of two different lines of cultured fibroblasts (FF302 and FF2209) showed identical production of these two bands. Cells treated with AdLacZ or saline failed to show any detectable levels of VEGF protein.

EXAMPLE 8

Human Skin Grafting

Serum immunoglobulin levels of SCID mice (CD17, The Wistar Institute, Philadelphia, Pa.) were verified to be <3.0 μg/ml at the age of 6 weeks by ELISA to ensure adequate immunodeficiency. The SCID mice (6–8 week old) were anesthetized with a ketamine (20 mg/cc)/xylazine (100 mg/cc)/acepromazine (10 mg/cc) cocktail and an elliptical 2–4 $cm^2$ full-thickness cutaneous defect was created on the dorsal torso as previously described [Soballe et al, 1996]. Human skin was obtained from abdominoplasty operations performed by a single surgeon and was used for grafting within 3–6 hours of excision. The human abdominal skin was cut into full-thickness elliptical grafts measuring approximately 2.0 cm×1.0 cm (n=30). Grafts were defatted and trimmed of excess subcutaneous tissue to the reticular dermal layer for an average thickness of 0.5 cm and sutured in place with a circumferential running stitch (3-0 silk).

Each cell suspension (0.8 cc) contained $10^6$ fibroblasts in a 10% DMEMIMatrigel mixture kept on ice until use to prevent premature gelling. One cell suspension mixture was used for each graft. Fibroblast cell suspensions were previously infected with Ad/VEGF, Ad/LacZ, or no virus (mock) as described in Example 7 above. Prior to closure of the running suture, 0.8 cc of either Ad/VEGF-infected, Ad/LacZ-infected, or mock-infected fibroblast cell suspensions or a saline control was pipetted into the pocket between the murine dorsal surface and the undersurface of the human graft (n=8 per group). The running suture was then completed and the grafts were covered with Vaseline Gauze fitted to the size of the graft. A semiocclusive dressing (Tegaderm, 3M, St. Paul, Minn.) was circumferentially applied to each animal and was removed after 7 days. Each cage contained at least one graft from each group. Mice were photographed and sacrificed at weeks 1, 2, 4, 6, 8, and 12 for histologic and immunohistochemical analysis of grafts.

At the above indicated time points mice were anaesthetized with anesthetic cocktail for photographic documentation of grafts, and then sacrificed by $CO_2$ inhalation. Skin grafts were dissected free from surrounding murine tissue down to and including the dorsal fascial layer. All specimens included surrounding areas of murine skin, so that histologic examination of the humanlmurine junction of the grafts would be possible Grafts were bisected both horizontally and vertically so that all areas of the graft could be examined. Half of the specimen was fixed overnight in 10% neutral buffered formalin at room temperature, properly processed, and embedded in paraffin. Replicate serial sections from each of the paraffin blocks were stained with hematoxylin and eosin. The other half of the grafts were embedded in OCT medium (Miles, Elkhart, Ind.), snap-frozen in liquid nitrogen, and stored at −70° C. Frozen sections were cryosectioned at 5 μm and used for immunohistochemical analysis.

Bisbenzimide trihydrochloride (Hoechst No. 33258), 4 mg/l, was applied for 1 minute to paraffin sections in order to establish the species of origin of cells in the grafts. Immunohistochemical analysis on frozen sections 3–8 microns) was performed using a sensitive Multilink Detection System (Biogenex, San Ramon, Calif.). Frozen sections were air-dried on positively charged glass slides, fixed in acetone at room temperature for 10 minutes at RT, then blocked with 10% goat serum for 10 minutes at 25° C. Slides were washed between each step in sterile phosphate-buffered saline [PBS], pH 7.4. Primary antibodies were placed over each section and incubated in a humidified chamber overnight at 4° C. After thorough rinsing with PBS, sections were overlayed with a biotinylated multispecies secondary antibody followed by thorough washing and application of label. The slides were rinsed well in PBS, and then developed with chromagen 3,3'-DAB and counter-stained with hematoxylin. Cell- and species-specific monoclonal antibodies were used to characterize the resident skin cell types participating in wound repair, the inflammatory response, and the proliferative potential of adenovirus-treated and control skin cells. The antibodies used in this study include monoclonal anti-human PECAM-1 and monoclonal anti-murine PECAM-1 to identify the endothelial cell and vessel species of origin. All sections were analyzed and photographed with a microscope.

The results of this grafting were as follows: The gross appearance of Ad/VEGF FF-treated grafts showed marked survival after one week as compared to controls. Appearance of these grafts was nearly identical at one week to that on day zero. Grafts treated with Ad/LacZ infected FF, mock infected FF, or saline had similar appearances at one week, which showed evidence of early graft failure in the form of epidermal necrosis and epidermal ulcerations. At two weeks, the Ad/VEGF FF-treated grafts began to exhibit signs of blotchy necrosis, however, control grafts revealed a greater extent of necrosis with nearly complete loss of the epidermis and papillary dermis. At four weeks, all grafts appeared the same grossly, exhibiting a thick superficial eschar indicating superficial dermal necrosis, regardless of previous treatment.

The grafts were examined histologically at 1, 2, 4, 6, 8, and 12 week timepoints. At one week all grafts showed a variable amount of epidermal necrosis and small foci of epidermal ulceration. There was variable necrosis of adnexal structures (hair follicles and eccrine glands). At the base of the grafts, there existed a marked difference in vascularity between the VEGF group and controls. Grafts treated with Ad/VEGF FF showed an increased number of small, mature vascular channels in comparison to controls and grafts treated with LacZ FF. Also observed in this group were collections of viable fibroblasts intermingled with neutrophils which appeared to have a more healthy appearance than those in the control groups.

At week two, all specimens showed nearly complete epidermal necrosis and pallor of the superficial dermis (early necrosis). There was an increase in the neutrophilic infiltrate and there existed no significant difference between groups in the vascularity in or around the grafts. Progressive dermal necrosis was observed at week four in all specimens. Early re-epithelialization was noted at the periphery of the ulcers. Re-epithelialization progressed at week 6 and was almost complete by week eight. At weeks eight and twelve, variable amounts of scar tissue was present in the upper portion of the dermis. Normal, viable human eccrine glands and hair follicles were also seen at these timepoints. Although all grafts eventually regained uniquely human adnexal structures, there was no significant difference between grafts treated with VEGF FF, LacZ FF, and other controls.

This example demonstrates the ability of adenovirus to mediate gene transfer to human skin. The human skin/SCID mouse chimera model demonstrated both the response of human tissue to adenoviral infection and the nature of the acute inflammatory response. The effects of adenoviral infection and transgene expression on the rate and quality of human wound healing were as follows Normal skin architecture is restored in the presence of adenoviral infection equivalent to non-infected controls. Despite an acute inflammatory response afier adenovirus injection, no demonstrable difference in the healing capabilities of wounded skin was observed, suggesting that adenovirus-mediated gene transfer for the acceleration of wound healing is feasible.

EXAMPLE 9

Adenovirus-Induced VEGF Expression in Human Skin Grafts Results in Rapid Hypervascularization Another, more recent experiment confirms that adenovirus-induced VEGF over expression in human skin results in a rapid and dramatic hypervascularization of the grafts, which was associated with endothelial cell migration, proliferation, and vessel formation.

Human 293 cells were maintained in DMEM supplemented with 10% FCS. WM239A human melanoma cells were cultured in MCDB 153 with 20% L-15 medium and supplemented with 2 mM Ca, 2% FCS and 5 $\mu$g/ml insulin. Human umbilical cord endothelial cells (HUVEC) were cultured in M199 medium supplemented with 10% FCS and endothelial cell growth supplement. For virus infection, WM239A cells were grown to 90% confluence and infected with either Ad/VEGF, Ad/LacZ at a multiplicity of infection of 20:1 or not infected in quadrupliate 96-well tissue culture plates for 2 hours. Culture supernatants had been preincubated for 1 hour at 22° C. with neutralizing mAb against either VEGF or monocyte chemoattractant protein-1 (anti-MCP-1) at 5 $\mu$g/ml. Cells were then washed and incubated in the absence of FCS for 72 hours, when the supernatant was collected for endothelial DNA replication assays. After 48 hours, cells in 0.9 $cm^2$ microliter wells were incubated with [$^3$H]-thymidine for 4 hours (1 $\mu$Ci/well) and assayed for incorporated radioactivity using a $\beta$-counter after growth of HUVEC in serum-free M199 media with endothelial cell growth supplement. All assays were done in quadruplicate in 2 independent experiments. Secretion of VEGF by transduced cells was quantitated using an ELISA kit (R&D Systems, Minneapolis, Minn.).

Western blot analysis for VEGF expression was performed using a mAb against recombinant human VEGF (R&D Systems). WM239A melanoma cells were infected with the adenoviral constructs either Ad/VEGF, or Ad/LacZ or not infected. Serum-free supernatants was collected after 72 hours. Samples (100 $\mu$l) were run on a 15% SDS-polyacrylamide gel under reducing or non-reducing conditions (ie., in the absence or presence of 2-mercaptoethanol). The gel was electroblotted to a PVDF membrane overnight at 40V and blocked for 2 hours with 2% BSA in PBS/0.05% Tween 20. The membrane was then incubated with a mAb reactive against VEGF.

Grafting experiments were performed as follows: Human neonatal foreskin contributed by area hospitals was used for grafting within 48 hours after removal. At age 8–12 wk, recombinase activation gene (Rag)-1 knockout mice, which have no mature B and T lymphocytes (the Wistar Institute Animal Facility) were anesthetized and 1–3 $cm^2$ full-thickness cutaneous defects were created on the dorsal torso [Juhasz, I, et al., 1993, *Am. J. Pathol.*, 143:528–537; Yan, H. C. et al, 1993, *J. Clin. Invest.*, 91:986–996]. Full-thickness human skin was sutured in place. Mice were used for experiments after 4–5 week, when grafts were well-healed. The human foreskin xenografts were injected once intradermally with 5×10$^8$ pfu/100 $\mu$l of either Ad/VEGF or Ad/LacZ. Mice from each group were sacrificed on days 3, 7, 14, 28, 35, and 49 for histological and immunohistochemical analysis of grafts.

Skin grafts were dissected free from surrounding murine tissue and bisected perpendicular to the long axis of the graft. Half of the graft was fixed overnight in 10% neutral buffered formalin at room temperature and paraffin-embedded. Replicate serial sections from each of the paraffin-embedded grafts were stained by hematoxylin and eosin (H&E). The other half of the graft was embedded in OCT medium and snap-frozen in liquid nitrogen. Tissue was prepared for immunohistochemistry by freezing in OCT embedding media (Miles, Elkhart, IN) and then cryosectioned at 5 $\mu$m.

Immunohistochemistry was performed on serial cryosections by immunoperoxidase technique [Juhasz et al, Yan et al; cited above] using an avidin-biotin-peroxidase complex system (Vector Lab., Burlingame, Calif.), and 3,3'-diaminobenzidine as a chromagenic substrate. Tissue sections were acetone-fixed for 10 minutes at 4° C. After thorough rinsing with PBS, sections were overlayed with biotinylated IgG anti-mouse or -goat IgG for 30 minutes at room temperature. After washing, avidin-biotin-peroxidase complex was added for 45 minutes. Slides were rinsed well in PBS, developed with 3,3'-diaminobenzidine and counterstained lightly with hematoxylin. Antibodies used in the study include mouse mAb against VEGF (R&D Systems), mouse mAb against human Ki67 proliferation marker (immunotech, Westbrook, Me.), and mouse mAb against either murine or human PECAM-1 (Dr. S. AMbelda, Philadelphia, Pa.)

The results of this experiment were as follows: Cells transduced with recombinant adenovirus Ad/VEGF were induced to produce or secrete biologically active VEGF.

When assessed by Western blot analysis after non-reducing SDS-PAGE, VEGF complexes of 36 kDa (glycosylated dimeric $VEGF_{121}$), 32 kDa (heterodimeric $VEGF_{121}$ containing one glycosylated monomer and one unglycosylated monomer), and 28 kDa (unglycosylated dimeric $VEGF_{121}$) secreted from WM239A melanoma cells or dermal fibroblasts. No detectable VEGF was released from Ad/LacZ or uninfected cells. Under reducing conditions, monomeric VEGF protein bands migrated only to 18 kDa (monomeric glycosylated $VEGF_{121}$) and 14 kDa (monomeric unglycosylated $VEGF_{121}$). The presence of different forms of $VEGF_{121}$ follows the documented expression of glycosylated and unglycosylated forms of $VEGF_{121}$.

As determined by immunoassays, infected cultures secreted the growth factor at 10 $\mu g/5\times10^5$ cells/ml over a 72-hour period. Secreted VEGF was biologically active, stimulating DNA synthesis of human umbilical cord endothelial cells more than two-fold and this activity was blocked by a neutralizing mAb to VEGF (FIG. 2).

The results of this experiment also demonstrate that Ad/VEGF induces hypervascularization in human skin. Histology and immunohistochemistry of lesions in human skin after Ad/VEGF injection produced the following results. Prior to injection, human neonatal foreskin grafted to immunodeficient Rag-1 mice was flat, flesh-colored, and smooth. At 3 days after injection of Ad/VEGF, sections of grafts showed raised, swollen endothelial cells bulging into newly formed vessels with wide lumina and dilated vascular spaces and intense erythema, resembling a hemangioma type lesion. These vascular structures were histologically indistinguishable from capillary hemangiomas. The dermis developed edema, and minimal hyperplasia of the epidermis was seen. The endothelial cell proliferation continued for at least 4 weeks. Swelling of the human skin graft subsided after 14 to 21 days. At 28 days after Ad/VEGF injection, the vascular spaces decreased in size and were lined by endothelial cells. The intense erythema was maintained for at least 28 days, gradually changing by 49 days to a pink color with glazed appearance. The glazed, scar-like texture of the skin was maintained for at least an additional 3 weeks (60 days). At 60 days the VEGF injected graft shows a reduction in the number of vessels with a thinning of the epidermis and loss of rete ridge structures indicative of scarring, edema is no longer apparent and fibroblasts have repopulated the graft. The histology of Ad/VEGF injected grafts revealed involution of the vascular neoplasm at 60 days with fibrosis and rejection in overall vessel numbers. Such involution resembles the natural resolution of hemogiomas.

Skin grafts injected with LacZ/Ad showed none of the clinical or histological features associated with hemangioma formation. In contrast, at 3 days after Ad/LacZ injection, grafts showed no increase in vessel formation and showed mild dermal edema with a mild mixed inflammatory infiltrate of mononuclear cells and neutrophils. Injection of control virus Ad/LacZ did not alter the appearance of the xenograft at any time after injection. The mouse skin during the experiment remained unchanged.

Immunostaining of sections of grafts 3 days after injection with Ad/VEGF revealed intense VEGF reactivity, whereas sections of control grafts injected with Ad/LacZ showed no such reactivity. The increased presence of murine endothelial cells relative to the Ad/LacZ injected graft was noted at 3 days No overall increase in the number of human vessels was seen between Ad/VEGF and Ad/LacZ injected grafts at 3 days, suggesting the quicker response of murine vessels from the surrounding mouse vasculature to VEGF. VEGF expression was detected mostly in the dermis, while epidermal keratinocytes did not stain with the VEGF mAb. Antibody staining for VEGF after infection of human skin grafts with Ad/VEGF diminished drastically by 14 days, while the lesions maintained their hemangioma appearance both clinically and histologically. By days 21 and 28, VEGF expression was no longer shown in the dermis of the graft. The increased vascularization in grafts injected with Ad/VEGF was due to proliferation of murine vessels which were visualized with a mAb against murine PECAM-1. Some murine vessels were also detected in the control group and also at day 0. No increase in human vessel proliferation was observed when comparing grafts injected with Ad/VEGF versus grafts injected with Ad/LacZ, using a mAb against human PECAM-1. The infiltration of murine vessels into human skin is probably due to the initial activation of murine endothelial cells and subsequent attraction of vessels expressing flk-1 [Millauer, B, et al, 1994, *Nature* (Lond.), 367:576–579] to the human skin which overexpresses VEGF. Chemoattraction by VEFG of vessels has previously been reported when KDR was stably expressed in porcine aortic endothelial cells [Waltenberg, J, et al, 1994, *J. Biol. Chem.* 269:26988–26995].

VEGF appeared to be expressed mainly by fibroblasts. This expression pattern may follow the natural pathology of hemangioma formation in that cultured neonatal hemangioma cells were found to secrete VEGF [Cohen, T. et al, 1996, *J. Biol. Chem.* 271:736–741].

Supernatant from VEGF/Ad transduced cells was shown to be mitogenic, this response was neutralized in the presence of a mAb towards VEGF.

This example demonstrates that targeted and focal expression of VEGF in human skin after intradermal injection of Ad/VEGF provides a suitable strategy for use as a model of neoangiogenesis. This model has advantages over the rabbit [Li, W. W. et al, 1991, *Invest. Ophthalmol & Visual Sci.*, 32:2906–2911] or rat [Fournier, G. A, et al., 1981, *Invest. Ophthalmos & Visual Sci.*, 21:351–354] corneal micropocket assays for angiogenesis or the chick chorioallantoic membrane assay [Brooks, P. C. etal, 1994, *Science*, 264:569–571] which are limited because of their relevance to human pathology. This model of vascular lesion formation in human skin also provides a model to understand the proliferation and involution of hemangiomas in infants.

EXAMPLE 10

AD/PDGF in Human Skin Xenografts and Normal Human Fibroblasts

In this example, a recombinant adenoviral vector containing the PDGF-BB gene (Example 1) was constructed and subsequently tested for its efficacy in producing biologically active PDGF-BB in human skin xenografis and normal human fibroblasts, as well as its ability to mediate gross changes in the skin.

A. PDGF-B Secreted by Transduced Human Cells Stimulates Growth of Fibroblasts

1. Determination of PDGF-B Production by WM239A Cells

WM239A melanoma cells, maintained in MCDB 153 medium with 20% L-15 medium supplemented with 2 mM $Ca^{2+}$, 2% FCS and 5 $\mu g/ml$ insulin, were grown to 90% confluence. The cells were then washed and incubated with Ad/PDGF or Ad/LacZ (Example 1), in the absence of FCS for 2 hours at a MOI of 20:1, a media control was also added. Fresh media with 10% FCS was then added to the cells for 24 hours, after which cells were incubated for 5 days in serum-free medium.

Western blot analysis was performed on supernatants (100 $\mu l$) from WM239A cells transduced with either Ad/PDGF, Ad/LacZ, or not infected and grown in serum-free media, at a density of 1×10⁶/10 ml/cm² tissue culture plate. The supernatants were subjected to electrophoresis in a 15% polvacrylamide gel, in the absence (non-reduced) or presence (reduced) of 2-mercaptoethanol The gel was electroblotted to a polyvinypyrolidone (PVDF) membrane, which was incubated with a 1:1000 dilution of goat polyclonal anti-human PDGF-B neutralizing serum (R and D Systems, Minneapolis, Minn.).

Figures 4A, 4B:
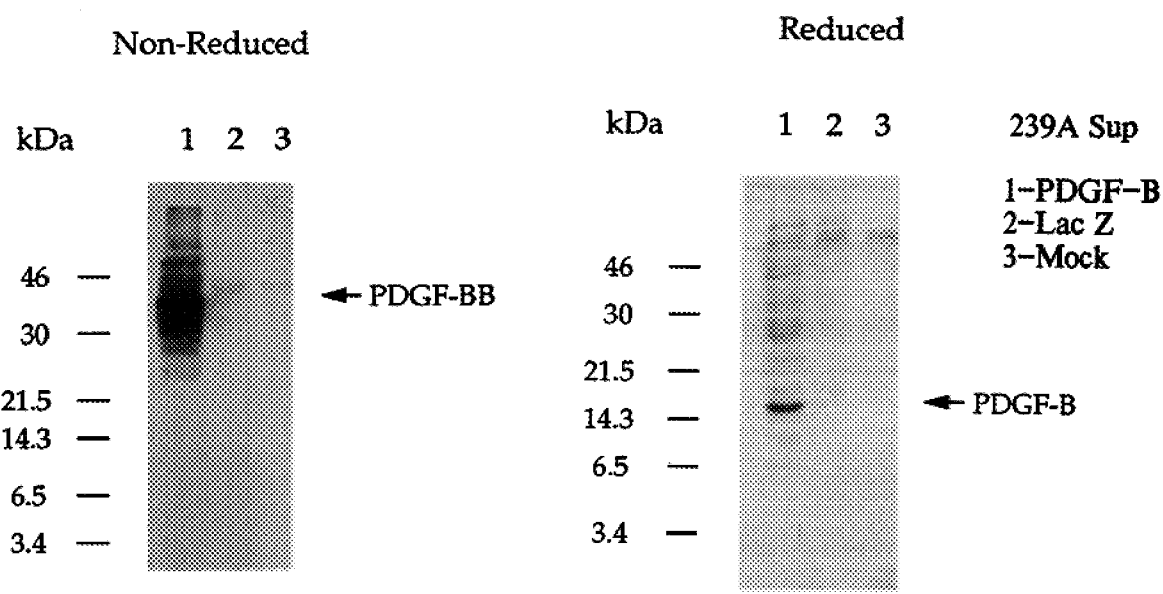
FIG. 4A is a Western blot of non-reduced PDGF-B/Ad5 supernatants from virally transduced WM-239A melanoma cells, using a goat serum specific for PDGF- B. Lane 1 is a WM-239A supernatant containing AdPDGF-B, lane 2 is a WM-239A supernatant containing a adenovirus vector carrying a β-galactosidase marker gene; lane 3 is a WM-239A mock-transfected supernatant. A PDGF-BB dimer migrating in the 30–37 Kda range in the non-reduced form is shown in lane 1.
FIG. 4B is a Western blot of the reduced supernatants of FIG. 4A. The lanes are the same as described for FIG. 4A. When reduced, monomeric PDGF-B migrates about 15 Kda.

WM-239A melanoma cells grown in tumor medium without FCS and transduced with Ad/PDGF is capable of producing functional PDGF-B protein. Western blotting depicted (FIG. 4A) an Ad/PDGF-supernatant displaying a PDGF-BB dimer migrating in the 30–35 Kda ran(ge, in the non-reduced form When the supernatant sample was reduced (FIG. 4B), monomeric PDGF-B is shown migrating about 15 Kda.

2. Growth Stimulation of NIH-3T3 Fibroblasts by PDGF-B Overexpressing WM239A Cells.

For calculation of secretion of PDGF-B by transduced cells, dilutions of culture supernatants were incubated with NIH 3T3 low passage murine fibroblasts [American Type Culture Collection (Rockville, Md.)], (which had been maintained in DMEM (Gibco/BRL, St. Louis, Mo.) supplemented with 10% heat-inactivated bovine serum (HyClone) and antibiotics), in the presence or absence of specific neutralizing antibody. Ad/PDGF-infected WM239A supernatants were pre-incubated at 22° C. for 1 hour with either goat anti-PDGF-B neutralizing serum (5 μg/ml) or rabbit anti-MCP-1 neutralizing serum (5 μg/ml). Ad/LacZ infected control WM239A supernatants were pre-incubated with either PDGF-B or MCP-1 neutralizing sera (5 μg/ml). 100 μl of recombinant PDGF-B (R&D) was pre-incubated with either goat anti-PDGF-B at 5 μg/ml or rabbit anti-MCP-1 at 54g/ml, and then incubated with cells for 24 hours.

NIH-3T3 fibroblasts (2×10⁴) were incubated in triplicate in 96 well plates with 100 μl of each WM239A serum-free supernatant at the dilutions: 1:1280, 1:640, 1:320, 1:160, 1:80, 1:40, 1:20, and 1:10. Cells were left for 24 hours and [³H]-thymidine incorporation into NIH 3T3 fibroblasts was measured by pulsing the cells for 4 hours with 1 μCi of [³H]-thymidine/0.9 cm² well of microtiter wells The thymidine incorporation induced by a given dilution of culture supernatant was transposed onto a standard curve derived from known concentrations of recombinant PDGF-BB. All assays were done in quadruplicate and repeated at least twice.

The mitogenic activity of culture supernatant from transduced cells was abolished by the addition of neutralizing anti-PDGF-B antibodies, whereas antibodies to the unrelated monocyte chemoattractive protein-1 (MCP-1) had no effect. Supernatants of cultures infected with a control adenovirus had no mitogenic activity. WM239A cell transduced with PDGF-B/Ad5 produced PDGF-BB at approximately 7.5 μg/ml/5×10⁵ cells over a 72 hour period.

Figure 5A:
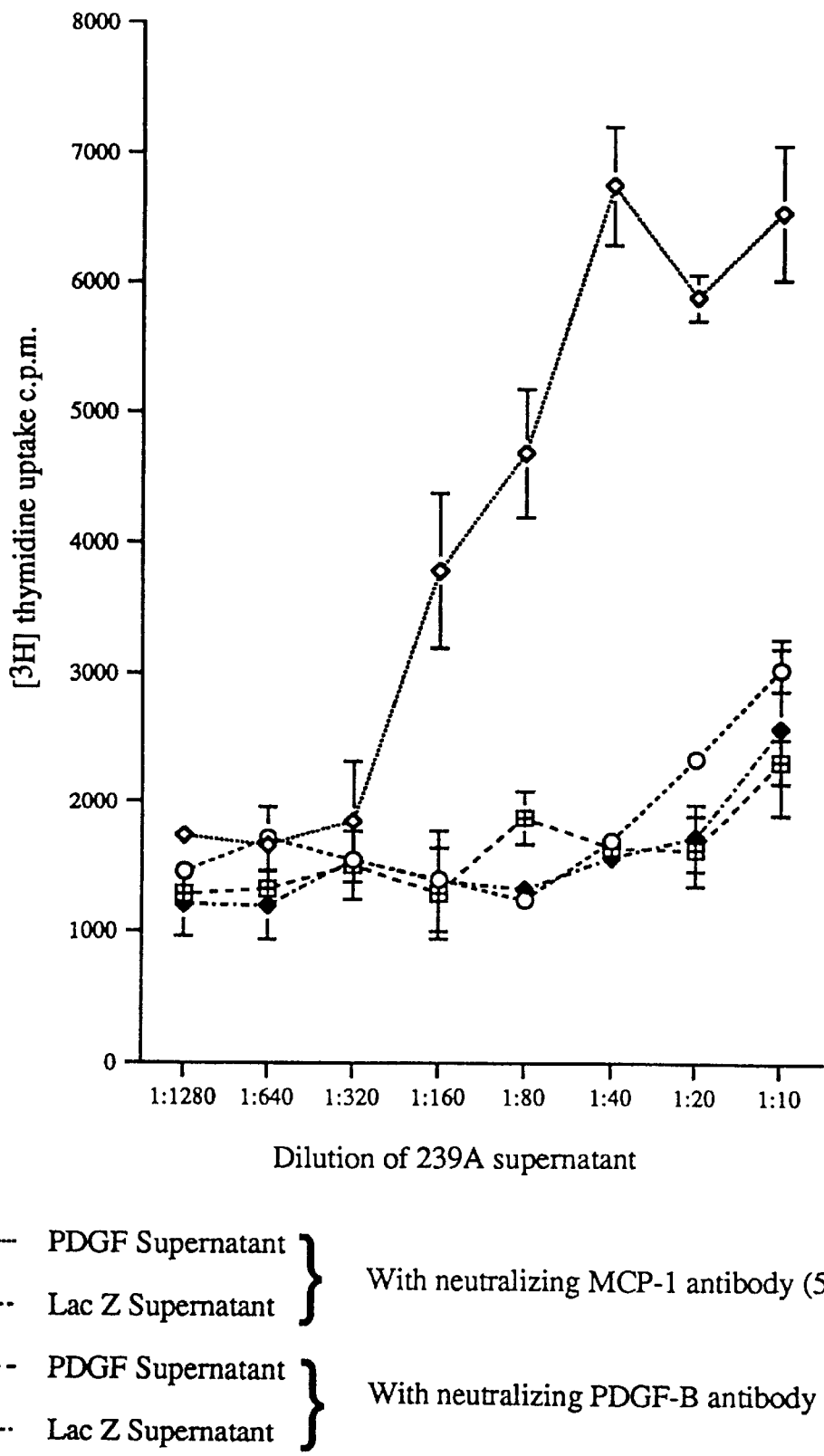
FIG. 5A is a graph of the results of a $[^3H]$ thymidine incorporation assay, plotting thymidine uptake vs. dilution of the supernatants of WM-239A cells transduced with adenovirus vectors as follows. The open triangle represents Ad/PDGF supernatant, the open circle represents Ad/LacZ supernatant, both pre-incubated with a non-specific neutralizing rabbit polyclonal sera (5μg/ml) against monocyte chemoattractant protein (MCP)-1. The square represents Ad/PDGF supernatant and the filled triangle represents Ad/LacZ supernatant, both pre-incubated with goat neutralizing antibody (5pg/ml) to PDGF-BB. The Ad/PDGF supernatant (open triangle) was found to maximally stimulate NIH-3T3 cells at a dilution of 1:40. The stimulation of NIH-3T3 cells was seen up to a dilution of 1:320. The level of $[^3H]$ thymidine incorporation for Ad/PDGF (square) was the same as that of the control supernatant from a Lac Z adenoviral (Lac Z/AdS) transduction of WM-239A cells, pre-incubated with either MCP-I or PDGF-BB neutralizing antibody.

In a [³H] thymidine incorporation assay, serum-free supernatants of transduced cells maximally stimulated NIH-3T3 mouse fibroblasts at a dilution of 1:40 when pre-incubated with a non-specific neutralizing rabbit polyclonal sera (5 g/ml) against monocyte chemoattractant protein (MCP)-1 (FIG. 5A). The stimulation of NIH-3T3 cells was seen up to a dilution of 1:320 (FIG. 5A).

Figure 5B:
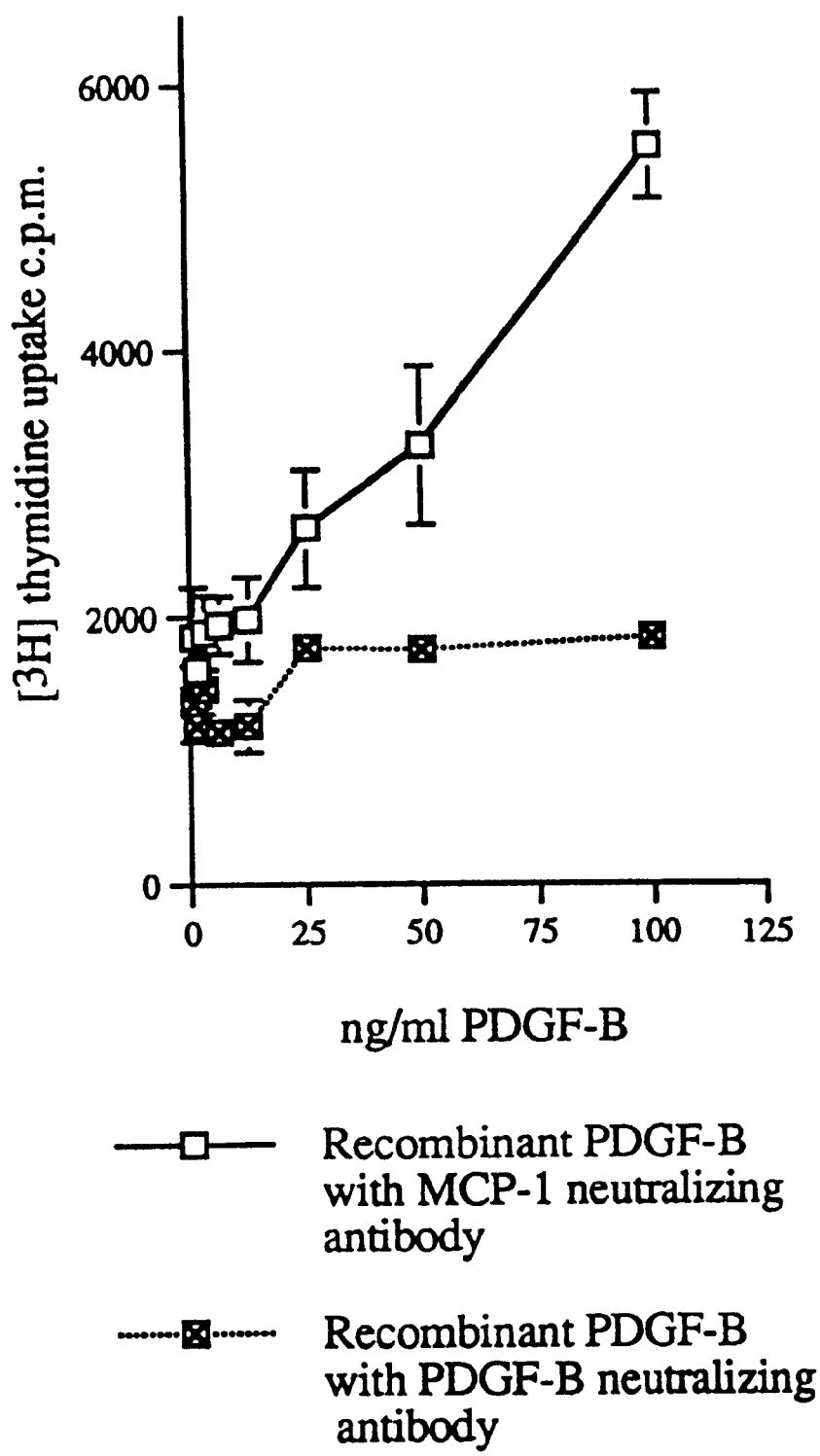
FIG. 5B is a graph of the results of $[^3H]$ thymidine uptake for PDGF-B/Ad5 supernatants diluted 1:80 or 1:160 and used on a standard curve from $[^3H]$ thymidine uptake of commercial recombinant PDGF-BB. The level of secretion of PDGF-BB was shown to be 7.5 μg/ml using a commercial ELISA kit® & D Co.).

In comparison, when supernatant obtained from PDGF-B transduced adenovirus was pre-incubated in the presence of a goat neutralizing antibody (5 μg/ml) to PDGF-BB, the level of [³H] thymidine incorporation was the same as that of the control supernatant from a Ad/Lac Z transduction of WM-239A cells, pre-incubated with either MCP-1 or PDGF-BB neutralizing antibody. When no antibody was used in blocking thymidine incorporation, the levels were the same as those for pre-incubation with MCP-1 antibody (data not shown). The level of secretion of PDGF-BB was shown to be 7.5 μg/ml, as ascertained from [³H] thymidine uptake for Ad/PDGF supernatants diluted 1:80 or 1:160 and used on a standard curve from [³H] thymidine uptake of commercial recombinant PDGF-BB (FIG. 5B).

3. Proliferation of Transduced Fibroblasts

The normal diploid human fibroblast cell line FF 2030, obtained from a human foreskin preparation [Cornil, I. et al, 1991, *Proc. Natl. Acad. Sci. USA*, 88:6028–6032], were transduced with Ad/PDGF or Ad/LacZ at a MOI of 20:1 for 2 hours in serum-free media. Cells were maintainined in DMEM with 10% FCS media. Initial FF2030 cell density was 1×10⁶/10 ml/10 cm² tissue culture plate. Plates were refed with DMEM 10% FCS media every 3 days. Growth of fibroblasts was visualized after 10–12 days using Dif-Quick stain [Saboorian, M. H. et al, 1997, *Cancer*, 81:187–192].

Normal human fibroblasts transduced with Ad/LacZ control virus show a flat morphology and cells remain contact inhibited despite regular medium changes. Parallel cultures infected with Ad/PDGF have a spindle, bipolar morphology, and cells have lost contact inhibition and grow in multiple layers.

Proliferation in a soft agar assay was determined as follows FF2030 fibroblasts were first infected with Ad/PDGF (MOI of 20:1), Ad/LacZ (MOI of 20:1), or mock and then trypsinized to a single cell suspension. Cells were then seeded at 3×10⁴ cells/well in a 6 well plate and resusupended in 2 ml 0.3% agar Noble (Difco), supplemented with 2% FCS and seeded in 35 mm wells containing 1 ml/well of 0.5% agar in 1×DMEM, 2% FCS. After 5 days, wells received 0.5 ml DMEM containing 2% FCS. After a further 5 days, colonies were counted (8 cells or more) in 10 microscopic fields. The average of 5 random fields at a x20 magnification was used to assess the number of colonies/field.

When transduced cells were grown anchorage independently in soft agar, fibroblasts expressing PDGF-B had a colony-forming efficiency of 8% whereas control cultures had colony-forming ability in less than 2% of cells. Colony size in PDGF-B-expressing cultures was 3- to 4-fold that of control cultures.

B. Human Skin Graft Experiments

Human neonatal foreskin contributed by area hospitals was used for grafting within 48 hours after removal. At age 8–12 wk, Rag-1 (Rag-1 /Rag-i ) mice [The Wistar Institute Animal Facility], were anesthetized and 1–3 cm full-thickness cutaneous defects were created on the dorsal torso. Full-thickness human skin was sutured in place. Mice were used for experiments after 4–6 weeks, when the grafts were well-healed. The human foreskin xenografts received a single intradermal injection of 5×10⁸ pfu/100 μl of either Ad/PDGF or Ad/LacZ. Individual mice also received a second injection after 2 weeks. Mice from each group were sacrificed at 3 days. 7 days, 14 days, 28 days, and 35 days for histological, histochemical and immunohistochemical analysis of grafts Skin grafts were dissected free from surrounding murine tissue and bisected perpendicular to the long axis of the graft Half of the graft was fixed overnight in 10% neutral buffered formalin at room temperature and paraffin embedded. Replicate serial sections from each of the paraffin embedded grafts were stained by hematoxylin and eosin, as well as Masson's trichrome stain. The other half of the graft was embedded in OCT medium and snap-frozen in liquid nitrogen. Tissue was prepared for immunohistochemistry by freezing in OCT embedding media (Miles, Elkhart, Ind.) and then cryosectioned at 5 nm.

Gross changes in skin was observed as follows. Human skin xenografts injected once with Ad/PDGF became raised with increased soft tissue growth after 3 days, when compared to their appearance after injection with Ad/LacZ, or prior to injection. After 7 days, grafts injected with Ad/PDGF remained raised, were erythrematous, and developed a glazed appearance at the site of hypertrophy. By 14 days, the skin grossly resembled either a normal translucent scar or a hypertrophic scar, with a persistent erythema at 21 days. In contrast, no gross changes in skin grafts injected with Ad/LacZ were apparent during the same time period.

Hypertrophic scarring of the human skin represents an abnormal response to wound healing. There is a resulting human fibroblast proliferation, with subsequent deposition of extracellular matrix proteins and reorganization of collagen. A limited amount of vessel formation also takes place. Soft tissue growth of the graft is seen very early, with phenotypic scarring of the graft occurring reproducibly within two weeks. These results show that PDGF-BB is responsible for the fibroplasia and limited aniogenesis seen within the formation of a hypertrophic scar.

To analyze histologic changes in the PDGF-B/Ad5 injected human grafts, sections were stained with H&E. At 3 days post PDGF-B adenoviral injection, skin sections show superficial edema, dermal hypercellularity, a mixed infiltrate of neutrophils and mononuclear cells, and irregular epidermal hyperplasia. The corresponding Ad/LacZ control group evidenced sparse inflammation, minimal epidermal hyperplasia, and sparse evidence of the mixed infiltrate. By 14 days following Ad/PDGF injection, the epitheliunm becomes thin with flattening of the rete ridge structures. The fibroblasts align parallel to the epidermis and inflammation is no longer apparent. These changes resemble an atrophic scar with epidermal atropny, flattened rete ridge architecture and spindled fibroblasts aligning parallel to the skin surface. The Ad/LacZ control group at 14 days shows irregular epidermal hyperplasia and mild edema with only a sparse mixed inflammatory cell infiltrate.

At 35 days post PDGF-B/Ad5 injection, increased cellularity is observed within the dermis in which the spindled fibroblasts are haphazardly arranged, which is not seen in controls. Both Ad/PDGF and Ad/LacZ-injected grafts maintain a low to moderate mononuclear cell infiltrate.

Immunohistochemistry was performed on serial cryosections by immunoperoxidase technique. Labeling was obtained using an avidin-biotinperoxidase complex system (Vector Lab., Burlingame, Calif.), and 3,3'diaminobenzidine (DAB) as a chromagenic substrate. Tissue sections were first acetone fixed for 10 minutes at 4° C., then primary antibody was placed over each section and incubated in a humidified chamber overnight at 4° C. The antibodies used in the study include goat polyclonal anti-PDGF (R&D Systems), mouse monoclonal anti-human Ki67 proliferation marker (Immunotech, Westbrook, Me.), and mouse monoclonal anti-fibroblast (proline-4hydroxylase) marker (Dako, Calpinteria, CA). After thorough rinsing with PBS, sections were overlayed with biotinylated IgG anti-mouse or anti-goat IgG for 30 minutes at RT. After washing, avidin-biotin-peroxidase complex was added at a concentration of 1100 for 45 minutes. The slides were rinsed well in PBS, and then developed with chromagen 3,3'-DAB and counterstained lightly with hematoxylin.

At 3 days post PDGF-injection and staining with rabbit anti-PDGF antiserum, grafts showed widespread staining of dermis (i.e., intense expression of PDGF-B) and no staining of epidermis (x4). The PDGF-B expression was confined to the dermis in proximity to the intradermal injection with minimal expression in the epidermis. In comparison the corresponding Ad/LacZ injected graft, which was stained with anti-PDGF antiserum showed a lack of PDGF expression (x4). Three day post AdtPDGF injection and collagen I and II staining with Masson's trichrome followed by counterstaining with H&E illustrated blue staining. Thus, Ad/PDGF injection resulted in a marked increase in extracellular matrix deposition as early as 3 days compared to the similarly treated Ad/LacZ control.

PDGF-B expression by 14 days was limited to scattered dermal fibroblasts and endothelial cells in the Ad/PDGF injected and stained cells. The dermal extracellular matrix continued to thicken, and by day 21 intense fibroplasia was observed as compared to the controls. 35 day post Ad/PDGF injection and staining for expression of the proliferation marker Ki67 revealed intense staining in the basal and suprabasilar layers of the epidermis with moderate staining in the dermis. This assessment of human cellular proliferation by K167 staining revealed a strong increase in proliferating keratinocytes, when the graft was injected with Ad/PDGF involving both basal and suprabasilar cells at 3 days, compared to the LacZ control injected graft at 3 days. The effect was less marked at 14 days but increased again at 35 days following a second injection of Ad/PDGF at 14 days. Despite the hypercellular appearance of the dermis, double labeling for dermal fibroblasts and expression of the proliferation marker Ki67 showed that only a few scattered human dermal fibroblasts were proliferating. In contrast, epidermal keratinocytes continued to rapidly proliferate which would suggest that part of the cellularity at the injection site may be due to either migration of human dermal fibroblasts to areas of PDGF-B overexpression, or proliferation of infiltrating mouse fibroblasts and inflammatory cells.

C. Conclusion

In both the fibroblast and skin graft experimental systems, growth occurred in a spatially and temporally restricted fashion. In xenografts gross morphological changes typically seen in healing wounds resulted from PDGF-B overexpression, with a final stage resembling scarring. Transduced fibroblasts were transiently transformed resulting in proliferation and the formation of benign fibroblastic lesions (fibromas) in immunodeficient mice. The fibromas regressed, which correlated with cessation of PDGF-B production. This example demonstrates that induction of endogenous expression of PDGF-B with adenoviral vectors accelerates the healing process in cutaneous wounds of the epidermal and dermal cells. This may be particularly important in chronic, non-healing wounds where PDGF is naturally poorly or not at all expressed.

Endogenous expression of PDGF-B in wounds may accelerate wound healing. Expression of PDGF-B resulted in a recapitulation of all of the processes involved in wound healing and production of normal translucent or hypertrophic scarring. Skin remodeling was induced that clinically and histologically resembles scarring as characterized by thinning of the rete ridges, and parallel reorganization of collagen structures. The target cells in human skin after intradermal injection are predominantly fibroblasts and endothelial cells. Very little infection of keratinocytes was seen, so that most of the effects derive from expression in fibroblasts. PDGF-B mediated both direct and indirect histological and morphological changes. At 3 days post adenoviral infection the direct effects were apparent. High levels of collagen were found on immunohistochemistry through trichrome staining, presumably accounting for the remodeling of the extracellular matrix protein seen after 3 days and consistent with increased collagen seen in hypertrophic scar formation.

Other histological changes most likely reflected the indirect effects of PDGF-B. Keratinocytes lack receptors for PDGF and the epidermal hyperplasia seen after 3 days may result from paracrine growth factor secretion from fibroblasts; candidate growth factors are most likely KGF or members of the EGF family such as EGF, TGFa, and HB-EGF. Similarly, increased angiogenesis or vascularization was presumably mediated by PDGF upregulating VEGF.

Expression of the proliferation marker Ki67 demonstrated proliferation. Importantly, the proliferative effects of PDGF were temporally restricted, with marked proliferation of dermal fibroblasts seen at 3 days reduced by 14 days, and no longer apparent by 35 days. Moreover, the histological changes following infection were confined to the site of adenovirus injection and did not involve the entire xenograft: the growth stimulus was spatially restricted. This circumscribed pattern of growth is distinct from that reported in the prior art, where PDGF overexpression in fibroblasts resulted in malignant transformation and fibrosarcomas in animals due to an autocrine growth stimulation [Yang el al, 1994, Carcinogenesis, 15:2167–2175, M. Pech et al, 1989, Proc. Natl. Acad. Sci. USA, 86:2693–2697].

PDGF-B secreted from transduced human cells is a dimeric molecule of 28–35 kDa which resolves itself upon reduction to a monomer of 15 kDa, in agreement with the predicted molecular weight for PDGF-B. The PDGF-BB dimer was found to be mitogenic for the growth of murine NIH-3T3 cells. The specificity of this proliferative response was shown when growth was ablated with a neutralizing antibody to PDGF-B. These results suggest an autocrine mechanism of transformation by stimulation of the PDGF receptor on fibroblasts. Fibroplasia was also seen when human dermal fibroblasts were transduced with PDGF-B/Ad5 and grown in culture. PDGF-B transduced human fibroblasts had a propensity to form colonies in soft agar (approximately 8%). The background level of about 1–2% in the controls is probably attributable to either serum in the soft agar, known to cause anchorage independent growth in soft agar, or clumping of cells in agar during seeding resulting in higher survival rates. The anchorage independent growth and dramatic increase in proliferation of normal diploid human fibroblasts, elicited by PDGF-B is indicative of the massive expression and transforming capability of PDGF-B.

This is the first demonstration, to our knowledge that PDGF-B can transform normal human fibroblasts. When the transduced cells were inoculated into animals, benign tumors well vascularized resulted, associated with a marked desmoplastic reaction; importantly, these regressed after 14 days. It is unlikely that a subpopulation of the cells formed tumors.

The PDGF-B adenovirus permits expression of the potentially therapeutically useful properties of PDGF in wound healing while circumventing the potential dangers of oncogenesis. Endogenous expression of growth factors in an adenoviral vector is a comparatively non-hazardous method for the delivery of potentially oncogenic growth factor genes to cells (predominantly fibroblasts) in chronic non-healing wounds.

EXAMPLE 11

Effect of AD/PDGF-B on Wound Healing in Animal Model

The ischemic rabbit ear model of impaired wound healing [S. T. Ahn et al, 1990, Ann. Plast. Surg., 24:17–23] is employed to test the effect of the PDGF-B gene, delivered by a replication deficient adenovirus, on the rate of wound closure, the duration of transgene expression, and the cell types infected by the adenoviral construct.

A. Ischemic Ear Wound Model

An ischemic ear was created in one ear of 10–12 week old female New Zealand white rabbits (Ace Animals) weighing 7–8 pounds [Ahn et al, cited above]. In brief, animals were anesthetized using Ketamine (60 mg/kg IM, Fort Dodge Labs, Fort Dodge, Iowa) and Xylazine (5 mg/kg IM, Phoenix Pharmaceuticals, St. Joseph, Mo.). The hair from both sides of each ear was shaved and the ears prepared with betadine. A circumferential incision was made I cm distal to the base of one ear down through the perichondrium. The rostral and caudal arteries were divided with 4-0 Vicryl suture (Ethicon, Somerville, N.J.) with preservation of the central artery and the rostral, caudal, and central veins. The circumferential incision was then closed with 5-0 Prolene suture (Ethicon). The wound was dressed with Tegaderm (3M Health Care, St. Paul, Minn.) and the animal allowed to emerge from anesthesia.

B. Effect of Recombinant Viruses acid PDGF-BB on Rabbit Fibroblasts

Rabbit ear fibroblasts were isolated using a modification of methods described in S. Goldstein et al, 1969, Diabetes, 18:545–549. One day following creation of the ischemic ear, rabbits were anesthetized and prepared as described above. A sterile surgical punch biopsy instrument (Miltex Instrument Co., Lake Success, N.Y.) was used to create two 6 mm wounds on the ventral surface of both the ischemic ear and the contralateral nonischemic ear. The biopsy tissue was extensively washed with PBS, placed dermis side down in 35 mm plates, and a microscope slide cover slip placed over the tissue to hold it in place. The tissue was incubated for 9 days in DMEM 10% FBS with changes of media every 3 days. At 10 days the tissue was removed and the plates incubated a further 3 days. Adherent fibroblasts were then removed by trypsinization followed by expansion through serial passage.

Passage 5 fibroblasts were grown to confluence in DMEM 10% fetal bovine serum (FBS, Gibco/BRL) and then incubated for 24 hours with 0, 1, 10, 50, 100, 250, or 500 PFU/cell of either recombinant virus Ad/LacZ or Ad/PDGF or vehicle as a control. Cells were then washed twice with PBS and then incubated in DMEM containing 1% Nutridoma (Boehringer Mannheim, Indianapolis, Ind.). After 24 hours the vehicle treated cells were stimulated with 0, 1, 10, or 100 ng/mL of PDGF-BB protein (Sigma). After 48 hours, the stimulated vehicle fibroblasts, the Ad/LacZ, and the Ad/PDGF infected fibroblasts were processed for proliferation assessment, total cellular RNA, or total protein.

C. Proliferation Assessment

Fibroblast monolayers treated with PDGF-BB protein, Ad/LacZ, or Ad/PDGF were incubated in DMEM 1% Nutridoma containing 1 $\mu$Ci/mL [$^3$H] thymidine. After 4 hours the supernatants were removed, the cells washed 2x with PBS, and the cells solubilized with 1% SDS 0.3 N NaOH. [$^3$H]-thymidine incorporation was measured on a Packard Scintillation Counter (Packard Intrument Company, Downers Grove, Ill.) All assays were done in quadruplicate. The resulting proliferation of rabbit fibroblasts infected with Ad/LacZ, Ad/PDGF, or stimulated with recombinant PDGF-BB protein are as follows: Minimal proliferation was stimulated with 0, 1, or 10 ng/mL of recombinant human PDGF-BB or with any PFU dose of Ad/LacZ. Stimulation with either 10 ng/mL of recombinant human PDGF-BB or 100 PFU Ad/PDGF resulted in significant increase in proliferation of the rabbit fibroblasts.

D. Total RNA

Total cellular RNA from the wounds mentioned above was isolated using Tri Reagent [Chomzynski (et al, 1987, Anal Biochem., 162: 156–159]. Briefly . 50–100 mg of tissue was homogenized in 1 mL of Tri Reagent and allowed to incubate at room temperature for 10 minutes. The aqueous and organic phases were split with the addition of 0.2 mL of chloroform and centrifuiged at 12,000 g for 15 minutes at 4° C. The upper aqueous phase containing the RNA was transferred to a 1.5 mL microfuge tube and the RNA precipitated with 0.5 mL of isopropanol followed by centrifugation at 12,000 g for 15 minutes at 4° C. The isopropanol was removed and the RNA pellet washed with 1 mL 95% ethanol followed by centrifugation at 7,500 g for 5 minutes at 4° C. The ethanol was removed and the RNA resuspended in diethyl pyrocarbonate (DEPC) treated water (Sigma).

E. Western Blot Analysis

Western blot analysis was performed on cell lysates from the rabbit fibroblasts infected as described above with increasing PFU of Ad/PDGF in non-reducing conditions as follows. Fibroblast monolayers were lysed using Tris lysis buffer, run on a nonreducing 12% polyacrylamide gel, and transferred to a nylon membrane by electroblotting. The membrane was blocked in PBS with 10% non-immune rabbit serum overnight at 4° C. and then incubated for 4 hours with a goat polyclonal antibody to human PDGF-BB (1:400, R&D Systems, Minneapolis, Minn.) in PBS containing 10% non-immune rabbit serum at RT. The membrane was washed 6 times with PBS containing 0.05 Tween and then incubated for 1 hour with a biotinylated horse anti-goat (1 400 dilution, Vector Lab., Burlingame, Calif.) for 1 hour at RT. The membrane was washed with PBS and then avidin-biotin complex (1:3000 dilution, Vector Lab) was added for 45 minutes at RT. The membrane was washed with PBS and developed with chromagen 3,3'-diaminobenzidine (Sigma).

The results of the Western blot are as follows: No human PDGF-BB protein was detected in the uninfected, 1, or 10 PFU Ad/PDGF/cell groups. However treatment with 100, 250, and 500 PFU of recombinant virus resulted in increased production of a 30 kD band corresponding to the size of purified PDGF-B, which was run in the control protein lane This band increased in a dose dependent fashion with increasing concentration of adenovirus F. Effect of Ad-PDGF-B on Wound Histology In another experimental protocol, after the creation of the 6mm wounds in the rabbits mentioned above, $10^6$ or $10^8$ particle forming units (PFU) of Ad/PDGF or Ad/LacZ in 50 μL of 20 mM Hepes/150 mM NaCl (pH 7.8) containing 10% glycerol, or vehicle control, was injected intradermally and circumferentially around the wound using a series 1700 Hamilton gastight 50 μL syringe and 30 gauge needle (Hamilton Company, Reno, Nev.). Injection of 5 μg of recombinant PDGF-BB (Sigma)/wound was also performed at the time of wounding for comparison. Following injection the wounds were dressed with Tegaderm.

At 3, 7, and 14 days after wounding, the wounds were harvested. Wound tissues were fixed overnight in 10% neutral buffered formalin at 4° C., bisected, and paraffin embedded or cryopreserved in 20% sucrose overnight at 4° C. followed by embedding in OCT media (Miles, Elkhart, Ind.) for frozen sectioning. For isolation of total cellular RNA full thickness skin down to perichondrium was excised in a 8 mm radius centered on the site of the original wound, snap frozen in liquid nitrogen, and stored at −80° C. for later RNA extraction.

For histological examination, serial 5 μm sections were obtained from each of the paraffin embedded wounds using a 30/50 microtome (Leica, Heerburgg, Switzerland). Sections were collected on Superfrost Plus slides (Fisher, Pittsburgh, Pa.) and stained with hematoxylin and eosin or with Masson's trichrome [P. Masson, 1929, J. Tech. Meth., 12:75–90]. On microscopic examination the epithelial gap, defined as the distance between encroaching epidermal elements, was measured using a stage micrometer (Leica). The student's t test was used for assessing differences in epithelial gap with a p<0.05 considered significant.

Results of the histological examinations are as follows. The ischemic rabbit ear demonstrated a significant defect in wound healing with minimal reepithelialization and absent granulation tissue when treated with vehicle alone. In contrast, the non-ischemic rabbit ear wound has reepithelialized almost 50% and has a modest amount of granulation tissue. Treatment with $10^6$ PFU of Ad/PDGF/wound resulted in a modest improvement in wound healing with partial reepithelialization and formation of a moderate amount of granulation tissue in both ischemic and non-ischemic wounds. Treatment with $10^8$ PFU of Ad/PDGF per wound resulted in a significant improvement in wound healing in the ischemic car with nearly complete reepithelialization and an exuberant amount of granulation tissue. Administration of $10^8$ PFU of Ad/PDGF per wound to the non-ischemic wounds resulted in modest granulation tissue and reepithelialization; however this was not significantly different from the vehicle treated wounds. One time administration of 5 μg recombinant human-PDGF-BB resulted in no difference in wound granulation tissue or reepithelialization compared to vehicle in either the ischemic or non-ischemic wounds. Treatment of both the ischemic and non-ischemic wounds with $10^6$ or $10^8$ PFU of Ad/LacZ also resulted in no improvement in wound reepithelialization or granulation tissue formation compared to vehicle.

The vehicle treated ischemic rabbit ear demonstrated a significant defect in reepithelialization, with an epithelial gap of 3.4±1 mm versus 2.3±1.4 mm in the non-ischemic vehicle, p<0.006. Treatment with 106 plaque forming units (PFU) of Ad/PDGF per wound resulted in a modest improvement in reepithelialization, with a decrease in the epithelial gap in both ischemic (1.9±1.8 mm, p<0.03 vs ischemic vehicle) and non-ischemic wounds (1.3±1.5 mm, p<0.07 vs non-ischemic vehicle). Treatment with $10^8$ PFU of Ad/PDGF per wound resulted in a significant improvement in wound reepithelialization in the ischernic ear, with a decrease in the epithelial gap to 0.7±1.1 mm, (p<0.00002). Administration of $10^8$ PFU of Ad/PDGF per wound to the non-ischemic wounds resulted in an epithelial gap of 2.8±0.1 mm, which is no different from the vehicle treated wounds. One time administration of 5 μg recombinant human Ad/PDGF resulted in no difference in wound closure compared to vehicle with an epithelial gap of 3±0.6 mm in the ischemic wounds and 2.6±0.1 mm in the non-ischemic wounds. Similarly, treatment with $10^6$ PFU of Ad/LacZ resulted in no improvement in wound healing with an epithelial gap of 4.1±2 mm in the non-ischemic wounds versus 5.1±1.1 mm in the ischemic wounds. Treatment with $10^8$ PFU of Ad/LacZ did not improve wound healing in ischemic (3.8±2.5 mm)or non-ischemic wounds (6.2±0.2 mm) as measured by the epithelial gap.

G. Detection of Human PDGF-BB Protein by Immunohistochemistry

Paraffin sections (5 μm) described in part E above were collected on Superfrost Plus slides and incubated for 24 hours at 55° C. Slides were deparaffinated by 30 minutes immersion in xylene followed by rehydration through a graded alcohol series to deionized water over 10 minutes and allowed to air dry completely. To enhance antigen retrieval, the slides were immersed in Tissue Unmasking Fluid (TUF, Ted Pella Inc, Redding, Calif.) and the placed in a microwave (Ted Pella Inc.) for 5 minutes on high power. Blocking with non-immune goat serum (1:20 dilution) was performed for 20 minutes at room temperature (RT) followed by a 12 hour incubation with polyclonal goat anti-human PDGF-B (R&D Systems) at 4° C. The slides were then washed with PBS followed by a second blocking step with methanol containing 0.3% hydrogen peroxide for 30 minutes at RT. Slides were rinsed with deionized water, then PBS, followed by incubation with biotinylated horse anti-goat (1:200 dilution, Vector Lab) for 30 minutes at RT. The slides were washed with PBS and avidin-biotin complex (1:100 dilution, Vector Lab) was added for 45 min at RT. The slides were rinsed well in PBS, developed with chromagen 3,3' diaminobenzidine (Sigma) and lightly stained with hematoxylin.

The results of this experiment show that ischemic wounds treated with vehicle demonstrated no specific immunohistochemical staining for human PDGF-BB protein at 7 days. The background staining is elevated in the vehicle treated wounds but is non-specific and likely related to the polyclonal nature of the primary antibody. In contrast, there was significant and specific staining for human PDGF-BB protein in the ischemic wounds treated with $10^8$ PFU Ad/PDGF. This staining appears to localize to fibroblasts participating in the wound healing response.

H. Localization of Ad-PDGF-B Infected Cells by In situ Hybridization

In situ hybridization for Ad/PDGF was performed on ischemic wounds three days after wounding. Polymerase chain reaction (PCR) was used to generate the biotinylated probes used in this experiment. In brief, the PstI/EcoRI fragment of the PDGF-B gene was used as a template for generating the probe. The PCR conditions were the same as described for PDGF-B in part H below, with the exception of the dNTP concentrations. The final concentration of dNTP's was 80 μM for dATP, dGTP, and dCTP with 52 μM for dTTP and 28 μM for Biotin-16-2'-deoxyuridine-5'-triphosphate (dUTP, Boehringer Mannheim). Following 30 cycles of PCR amplification the PCR product was separated from unincorporated nucleotides using a G-50 sephadex spin column (Boehringer Mannheim).

Paraffin sections (4 μm) as described above were collected on Superfrost Plus slides incubated for 24 hours at 55° C. Slides were deparaffinated by minutes immersion in xylene followed by rehydration through a graded alcohol series to deionized water over 10 minutes and allowed to air dry completely. Slides were then treated with proteinase K (10 μg/mL, Boehringer Mannheim) for 30 minutes, washed in PBS, and then post-fixed in 4% paraformaldehyde.

Sections were covered with hybridization solution containing biotinylated DNA probe prepared as described above, and 50% formamide. Slides were heated for 10 minutes at 95° C. and then incubated overnight in a humid chamber at 37° C. to allow hybridization. Four posthybridization washes in 1×SSC were performed for 15 minutes at 50° C. The slides were then incubated for 30 minutes at RT in 0.1M Tris-buffered saline (TBS pH 7.4) containing 0.1% bovine serum albumin (Sigma) and 1 mM levamisole (Sigma) to block non-specific binding. Streptavidin-alkaline phosphatase conjugate (1:75 dilution, Amersham) was added to the slides for 30 minutes at 37° C. Slides were washed with 0.1 M TBS for 20 min at RT. Bound streptavidin-alkaline phosphatase conjugate was detected by incubating the slides at 37° C. in alkaline phosphatase substrate solution (Gibco/BRL) for 2 hours. Slides were counterstained in nuclear fast red 1% (Sigma) and then washed with deionized water. The sections were dehydrated in graded alcohol over 10 minutes and then coverslipped.

Ischemic wounds treated with vehicle resulted in no in situ hybridization signal. In contrast, ischemic wounds treated with $10^8$ PFU AdCMV-PDGF-B demonstrated significant in situ hybridization. Once again it appears that the cells that have a positive in situ signal are fibroblasts that are participating in the wound healing response.

1. Duration of Transgene Expression by RTPCR and Dose Response of Ad-PDGF-B in Rabbit Fibroblasts For reverse transcriptase reaction, first strand cDNA was prepared from 1 μg total cellular RNA isolated above, using the procedure described by Sambrook et al., cited above. In brief, log of total cellular RNA in 9 μL total volume was added to each 0.65 mL microcentrifuge tube and placed on ice. A master mix was prepared and added on ice such that the final concentration of reagents for each sample was 200 U Moloney Murine Leukemia Virus Reverse Transcriptase (Gibco/BRL), 40 U RNAsin (Promega), 100 pmol of random hexamers (Boehringer Mannheim), 1 mM DTT, 500 μM deoxytriphosphates (Gibco/BRL), 50 mM KCl, 10 mM Tris-Cl (pH 8.3 at 22° C.), 2.5 mM NgCl$_2$, and 0.01% gelatin. After 1 hour at 37° C. the reverse transcriptase reaction was heat inactivated by incubation for 5 minutes at 94° C. After 1 hour at 370 C the reverse transcriptase reaction was heat inactivated by incubation for 5 minutes at 94° C.

Specific primers for human PDGF-B and rabbit B-actin were selected based on the published human PDGF-B cDNA [Collins et al, cited above] and rabbit B-actin cDNA sequences [D. Sakai el al, 1995, Bone, 17:111–119]. The human PDGF-B primer pair used was upstream primer 5'TGGGCGCTCTTCCTGTCTCTC [SEQ ID NO: 1] and downstream primer 5'CTCGGCCCCATCTTCCTCTCC [SEQ ID NO: 2] resulting in a 165 base pair product. The rabbit B-actin primer pair used was upstream primer 5'-TGGGCAGAAGGACTCGTA [SEQ ID NO: 3] and downstream primer 5'-CGCAGCTCGTTGTAGAAG [SEQ ID NO: 4] resulting in a 144 base pair product. PCR was performed on aliquots of the first strand cDNA prepared above using a modification of previously described methods [G. Gilliland et al, 1990, Proc. Natl. Acad. Sci. USA, 87:2725–2729]. In brief, 5 μL of the reverse transcriptase reaction was added to each 0.65 mL microcentrifuge tube and placed on ice. A master mix was prepared and added on ice such that the final concentration of reagents for each sample was 2.5U Amplitaq Gold DNA polymerase (Perkin Elmer, Norwalk, Conn.), 200 μM deoxytriphosphates (dNTP's, Pharmacia, Piscataway, N.J.), 50 mM KCl, 10 mM Tris-Cl (pH 8.3 at 22° C.), 1.5 mM MgCl$_2$, 0.01% gelatin, and 1 μM upstream and downstream primers. The samples were kept on ice until the thermocycler block (Hybaid Limited, Manchester, United Kingdom) was at 94° C., when the samples were immediately placed into the block for 9 minutes. Samples were amplified for 30 cycles of 30 seconds at 94° C. followed by 30 seconds annealing at 58° C. for PDGF-B or 54° C. for B-actin followed by 1 minute of extension at 72° C. Upon completing the final cycle, samples were incubated for 5 minutes at 72° C.

RT-PCR analysis for human specific PDGF-B and rabbit specific β-actin was performed on ischemic and nonischemic wounds treated with $10^6$ and $10^8$ PFU Ad/PDGF at 3 and 7 days. Significant amounts of human PDGFB were detected at 3 days in both the ischemic and non-ischemic wounds. By 7 days, very little human PDGF-B mRNA is detected in both ischemic and non-ischemic wounds receiving I O6 or $10^8$ PFU Ad/PDGF. This is consistent with clearance of adenovirus from the wounds. There was no significant difference in rabbit β-actin controls.

RT-PCR analysis for human specific PDGF-B and rabbit specific β-actin was also performed on $10^6$ rabbit ear fibroblasts infected with increasing PFU of AdCMV-PDGF-B. No human PDGF-B mRNA was detected in rabbit fibroblasts that were not infected with the PDGF-B adenovirus or in fibroblasts infected with 0.1 PFU Ad/PDGF per cell. It is not until the concentration of 1 PFU Ad/PDGF per cell is used, that human PDGF-B MRNA was detected. The plateau production of human PDGF-B mRNA occurred between 50 and 100 PFU Ad/PDGF per cell. No difference in rabbit β-actin mRNA was detected.

EXAMPLE 12
Response of Skin to Adenovirus

The effects of adenovirus on human skin in vivo and of local adenovirus infection on wound healing are currently unknown [E. Fenjves, 1994, *Soc. Invest. Dermatol.*, 103:70s–75s; E. Fenjves et al, 1994, *Human Gene Ther.*, 5:1241–1248: H. Veelken et al., 1994, *Human Gene Ther.*, 55.1203–1210]. The effect of adenovirus infection in human skin in vivo and on wound healing was evaluated using a LacZ reporter gene in the human skin/SCID mouse chimera model. The human skin/SCID mouse chimera has been shown to demonstrate a normal rate and quality of dermal and epidermal skin repair [H. Lorenz et al., 1992, *Development*, 114:253–259,1 Juhasz et al., 1993, *Am. J. Pathol.*, 143: 1458–1469]. The absence of a normal B and T cell complement allows the SCID mouse to accept human skin xenografts without rejection [Boosma and Carroll, 1991, *Annu. Rev. Immunol*, 9:323–350]. Despite lacking a full humoral and cellular immune response, the SCID mouse does mount a normal acute polymorphonuclear and mononuclear response to surgical wounding [Juhasz et al., cited above; H- C. Yan et al., 1993, *J. Clin. Invest.*, 91:986–996; H- C. Yan et a/, 1994, *J. Immunol.*, 152:3052–3063].

A. Xenograft Preparation

Human skin was obtained from aborted products of conception between 18 and 24 weeks of gestation. Skin was trimmed of subcutaneous fat and then cut into circular grafts measuring 15–20 mm in greatest diameter. Severe combined immunodeficient mice (SCID-C57BL6) between 4–6 weeks of age were anesthetized using inhaled Metofane. Full-thickness skin grafts were transplanted into full-thickness size-matched wound beds prepared on each flank of the SCID mice. The grafts were surgically secured using 6 interrupted sutures of 6-0 polypropylene (U.S. Surgical, Norwalk, Conn.). Each graft was allowed three to four weeks for stable engraftment prior to experimental manipulation.

B. Characterization of Adenovirus Infection of Human Skin Grafts.

To determine the efficacy and distribution of adenovirus-mediated gene transfer to human skin in vivo and the subsequent inflammatory response, twenty human skin grafts on 10 SCID mice were injected intradermally using a 1700 Hamilton gastight 50 µl syringe and 30 gauge needles (Hamilton Company, Reno, Nev.): 10 grafts on five SCID mice were injected with $1\times10^8$ pfu of Ad/LacZ (Example 1) in 50 µl 20 mM HBS at pH 7.8, another 10 grafts received injections of vehicle, HBS at 50 µl, as controls. Confirmation of injection was evidenced by the presence of an epidermal wheel The area of injection was marked with indelible ink. Two days following injection, mice were sacrificed and grafts were harvested and processed for histology and immunohistochemistry.

C. Wound Healing and Adenoviral Infection.

To determine the effect of adenoviral infection and transgene expression on the response of human skin to surgical wounding, ten SCID mice bearing 2 human skin grafts were surgically wounded using a 2-mm trephine (Miltex Instrument Co., Lake Success, N.Y.). The site of wounding was marked in the base of the wound with India ink to assist in localization of the wound on histologic evaluation. Each wound margin was injected intradermally with either $1\times10^8$ pfu of Ad./LacZ in 50 µl HBS (n=10), or 50 µl of HBS alone (n=10). Approximately I 0 PI were administered via 3 separate injections around the wound margin, and 20 µl was placed on top of the wound bed. Two grafts of both virus-treated and control wounds were harvested and processed at time points of t=1, 3, 7,10, and 14 days post wounding.

D. Tissue Processing

Skin grafts were dissected free from surrounding murine tissue and bisected perpendicular to the long axis of the graft. Half of the graft was fixed overnight in 10% neutral buffered formalin at 4° C. and paraffin embedded for histological assessment. The other half of the graft was cryopreserved in 20% sucrose overnight at 4° C. Tissue was prepared for immunohistochemistry by freezing in OCT embedding media (Miles, Elkhart, Ind.) and then cryosectioned at 5 µm.

E. Histologic Assessment

Replicate serial sections (5 mm) from each of the formalin fixed and paraffin embedded wounded grafts were stained by hematoxylin and eosin (H&E), Masson's trichrome stain, and X-gal. The rate of healing of each graft was assessed histologically by examination of tissue sections. Each wound was evaluated histologically for the amount of inflammation and cellularity present during the early phases of wound healing. Wound closure was defined as completed re-epithelialization over a bed of granulation tissue. At the time of wound closure the grafts were assessed for the amount of granulation tissue present and the degree of cellular proliferation. Later comparable time points were analyzed for the amount of provisional matrix deposition and scar formation.

F. β-galaciosidase Histochemistry

Cryosections were fixed in 0.5% gluteraldehyde for 10 min, followed by rinsing twice in 1 mM $MgCl_2$/PBS for 10 minutes each. Slides were then incubated for one hour in the dark at 37° C. in β-galactosidase incubation solution containing 1µM $MgCl_2$, 20×KC solution in PBS at pH 7.4, and β-galactosidase (5-bromo-4-chloro-3indolyl β-D-galactopyranoside) at a final concentration of 1 mg/ml. Slides were then washed 3 times in tap water, counterstained with hematoxylin, and mounted for microscopic examination.

G. Immunohistochemistry

Immunohistochemistry was performed on serial cryosections (5 µm) by immunoperoxidase technique (Auhasz et al., 1993; Yan et al, 1993). Labeling was obtained using an avidin-biotin-peroxidase complex system (Vector Lab, Burlingame, Calif.) and 3,3'-diaminobenzidine (DAB) as a chromagenic substrate. Briefly, tissue sections were acetone fixed for 10 minutes at 4° C., then primary antibody (see below) was placed over each section and incubated in a humidified chamber overnight at 4° C. After thorough rinsing with PBS, biotinylated species-specific secondary antibodies were then applied for 30 min at room temperature. After washing, avidin-biotin-peroxidase complex was added at a concentration of 1:100 for 45 minutes. The slides were then rinsed well in PBS and developed with chromagen 3,3'-DAB and counterstained lightly with hematoxylin. Antibodies used were: anti-human CD31 (PECAM 1) from Dako Corp.); antihuman CD45 and Mac 3 (Novocastra); anti-mouse CD45 and Mac 3 (Pharmingen); anti-human Ki-67 (Coulter Corp.), additional monoclonal antibody specific for murine PECAM (Dr. S. Albelda, University of Pennsylvania).

1. Results

Intradermal injection of $1\times10^8$ pfu Ad/LacZ in intact human skin resulted in widespread gene transfer in proximity to the site of injection as indicated by X-gal staining two days following injection, which was absent in control skin xenografts. Dermal fibroblasts and endothelial cells showed intense β-galactosidase activity, whereas suprabasilar keratinocytes show little expression Despite sporadic transfection of suprabasilar keratinocytes, gene transfer was largely confined to the dermis and appeared to be limited by the basement membrane. Cell and species-specific immunostaining revealed predominant expression by murine endothelial cells in the vasculature of the dermis. Human endothelial cells were also identified, although less frequently.

There was a significant baseline inflammatory cell infiltrate in the skin xenotransplants prior to further manipulation. The cellular elements were predominantly acute inflammatory cells of murine origin. A marked increase in the inflammatory response was noted with adenoviral infection two days following injection. Immunostaining for the CD45 antigen was most pronounced in those areas expressing the greatest concentration of 13-galactosidase. The infiltrate was a mixed cellular response (CD45) with a high percentage of mononuclear cells (MAC-3). Species-specific immunostaining revealed the infiltrate to be almost exclusively murine with only rare human tissue macrophages identified. There was no detectable difference in cellular proliferation between virus and vehicle-treated grafts as indicated by the human proliferation marker Ki-67. Proliferation occurred most strongly along the basement membrane of the epidermis and in the germinal tissue of hair follicles and sweat glands in both groups.

In grafts in which a 2 mm excisional wound was created and then injected with Ad/LacZ, β-galactosidase expression was present two days following injection throughout the wounded dermis and at the leading edge of re-epithelialization. At 2 days post wounding and injection, the inflammatory response consisted of polymorphonuclear and mononuclear cells in both adenovirus and buffer-injected wounds. There was no detectable difference in the amount of inflammation present in adenovirus-treated grafts compared to control-wounded grafts.

All adenovirus-treated and control wounds were closed and healed by 7 days post wounding In grafts which were examined within the first 7 days after wounding, an area of hypercellular granulation tissue was observed in the center of the wound bed. This finding contrasted with adjacent areas outside the wound bed which predominantly demonstrated extracellular matrix proteins. There was no histologic difference in the quality of dermal fibroplasia present in either adenovirus-treated or control wounds by seven days post wounding. Each showed a fibrillar pattern of extracellular matrix (ECM) deposition. Also, both adenovirus and control grafts reconstituted a normal multi-layered epidermis.

At 14 days post wounding, all adenovirus-treated and control grafts showed deposition of the extracellular matrix protein collagen type I in the wound cleft. This effect continued in the formation of a scar up to 21 days post wounding in both groups. Similar results were seen for collagen type III.

The results of this example demonstrate that there is no detrimental effect of adenoviral infection on the normal process of wound healing in human skin in the SCID mouse model. Normal skin architecture is restored in the presence of adenoviral infection equivalent to non-infected controls. Despite an acute inflammatory response after adenovirus injection, no demonstable difference in the healing capabilities of wounded skin was observed. Adenovirus infection does not adversely affect the normal temporal sequence of wound healing despite an exacerbation of the acute inflammatory response. The endpoints of tissue repair including re-epithelialization, extracellular matrix deposition, and wound closure were established at an equal rate and to an equivalent degree between adenovirus- and vehicle-treated wounds. Wound closure, as measured by the time to re-epithelialization, occurred at 7 days in both experimental groups. Similarly, the amount of granulation tissue, degree of cellularity and cellular proliferation were the same in adenovirus-treated and control wounds The predominant extracellular matrix proteins human type I and type III collagens were also reconstituted normally in both groups. These results suggest that the use of adenovirus as a vector for induction of endogenous expression of growth factor would not adversely effect wound healing.

A fully immunocompetent animal would be expected to respond in the same manner to surgical wounding in the presence of adenovirus infection, given that the acute inflammatory response largely directs the process of wound closure. The development of a specific humoral or cell-mediated immune response is not expected to alter the wound healing process.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A method for enhancing the closure of a wound in mammalian skin, said method comprising
injecting directly into the dermis within the wound or underlying the wound, and thereby infecting fibroblasts in the dermis with, a composition consisting essentially of a recombinant replication defective virus in a buffer solution, said virus comprising a DNA sequence encoding a growth factor selected from the group consisting of a platelet derived growth factor and a vascular endothelial growth factor, under operative control of regulatory sequences which direct the expression of said DNA sequence,
wherein said infected fibroblasts produce said growth factor at levels sufficient to enhance closure of said wound.

2. The method according to claim 1, wherein said vascular endothelial factor is $VEGF_{121}$.

3. The method according to claim 1, wherein said platelet derived growth factor is selected from the group consisting of PDGF-B and PDGF-A.

4. The method according to claim 1, wherein said virus is an adenovirus.

* * * * *

UNITED STATES PATENT AND TRADEMARK OFFICE
CERTIFICATE OF CORRECTION

PATENT NO.    : 6,486,133 B1
DATED         : November 26, 2002
INVENTOR(S)   : Meenhard Herlyn et al.

It is certified that error appears in the above-identified patent and that said Letters Patent is hereby corrected as shown below:

Title page,
Item [56], References Cited, FOREIGN PATENT DOCUMENTS, insert
-- WO 93/13807    7/1993 --.

Column 2,
Line 11, replace "VEGF-B" with -- VEGF-β --.
Line 24, replace "VEGF-11" with -- VEGF-II --.
Line 34, replace "J. Muehihauser et al," with -- J. Muhlhauser et al --.
Lines 51 and 52, replace "[see, also, R. Ziegelstein et a/ 1994, Circul., 90(4), part II, p. 1899]." with -- [see, also, R. Pili et al, 1994, *Circul.*, 90(4), part II, P. 1147].
Line 62, replace "PDGFB" with -- PDGF-β --.

Column 3,
Line 67, replace "*Sur2.*," with -- *Surg.*, --.

Column 4,
Line 11, replace "91:21188-12192" with -- 91:12188-12192 --.
Line 12, replace "76-84s;" with -- 76s-84s; --.

Column 5,
Line 17, replace "grwoth" with -- growth --.
Line 29, replace "usin,," with -- using --.

Column 6,
Line 1, replace "(5pg/ml)" with -- (5μg/ml) --.
Line 7, replace "(Lac Z/AdS)" with -- (Lac Z/Ad5) --.

Column 7,
Line 61, replace "AdS" with -- Ad5 --.

Column 8,
Line 12, replace "d17OO1" with -- d17001 -- .

UNITED STATES PATENT AND TRADEMARK OFFICE
CERTIFICATE OF CORRECTION

PATENT NO. : 6,486,133 B1
DATED : November 26, 2002
INVENTOR(S) : Meenhard Herlyn et al.

It is certified that error appears in the above-identified patent and that said Letters Patent is hereby corrected as shown below:

Column 9,
Line 46, replace "10 pi" with -- 10 μl -- .
Line 48, replace "1x10 to 1x10$^{12}$" with -- 1x10$^4$ to 1x10$^{12}$ --.

Column 10,
Line 37, replace "iEi" with -- in --.
Lines 61 and 62, replace "angio (lenic disorders," with -- angiogenic disorders, --.

Column 12,
Line 16, replace "TGF-P" with -- TGF-β -- .

Column 13,
Line 21, replace "(Ads) with -- Ad5 -- .
Line 23, replace "usin (g conventional techniques" with -- using conventional techniques. --.
Line 29, replace "subcioned" with -- subcloned --.
Line 48, replace "AdS" with -- Ad5 --.
Line 63, replace "2%/o" with -- 2% --.

Column 14,
Line 10, replace "BarnHI," with -- BamHI, --.
Line 21, replace "(pfti)" with -- (pfu) -- .
Line 49, replace "DMNEM" with -- DMEM --.
Line 55, replace "MM" with -- mM --.

Column 16,
Line 14, replace "iii situ" with -- in situ --.
Line 15, replace "with" with -- which --

Column 17,
Lines 21 and 31, replace "B3" with -- β3 --.
Line 29, replace "PECAMi" with -- PECAM --.
Line 42, replace "VE(C1" with -- VEGF --.
Line 67, replace "8 pg/ml." with -- μg/ml. --

UNITED STATES PATENT AND TRADEMARK OFFICE
CERTIFICATE OF CORRECTION

PATENT NO. : 6,486,133 B1
DATED : November 26, 2002
INVENTOR(S) : Meenhard Herlyn et al.

It is certified that error appears in the above-identified patent and that said Letters Patent is hereby corrected as shown below:

Column 18,
Line 53, replace "wound the and" with -- the wound and --.

Column 19,
Line 11, replace "DNIM" with --DMEM --.
Line 16, replace "el." with -- gel. --.
Line 45, replace "(CD 17," with -- (CD 17; --.
Line 61, replace "DMEMIMatrigel" with -- DMEM/Matrigel --.

Column 20,
Line 7, replace "(Tegaderm, 3M," with -- (Tegaderm; 3M, --.

Column 22,
Line 1, replace "microliter" with -- microtiter -- .
Line 63, replace "(Dr. S. AMbelda, Philadelphia, Pa.)" with -- (Dr. S. Albelda, Philadelphia, Pa.) --.

Column 24,
Line 18, replace "VEFG" with -- VEGF --.

Column 25,
Line 2, replace "$1x10^6/10$ ml/cm$^2$" with -- $1x10^6$ ml/l0 cm$^2$ --.
Line 4, replace "polvacrylamide gel" with -- polyacrylamide gel --.
Line 5, replace "2-mercaptoethanol The" with -- 2-mercaptoethanol. The --.

Column 35,
Line 42, replace Yan et a/," with -- Yan et al, --.

Column 36,
Line 16, replace "I 0PI" with -- 10µl --.

UNITED STATES PATENT AND TRADEMARK OFFICE
CERTIFICATE OF CORRECTION

PATENT NO.   : 6,486,133 B1
DATED        : November 26, 2002
INVENTOR(S)  : Meenhard Herlyn et al.

It is certified that error appears in the above-identified patent and that said Letters Patent is hereby corrected as shown below:

Column 37,
Line 33, replace "13-galactosidase." with -- β-galactosidase. --.

Signed and Sealed this

Seventeenth Day of August, 2004

JON W. DUDAS
*Acting Director of the United States Patent and Trademark Office*